(12) United States Patent
Gehling et al.

(10) Patent No.: US 8,962,575 B2
(45) Date of Patent: Feb. 24, 2015

(54) CLERODANE DERIVATIVES FOR MODULATION OF LEUKOTRIENE RECEPTOR ACTIVITY AND RELATED DISEASES

(75) Inventors: Matthias Gehling, Leichlingen (DE); Torsten Grothe, Bochum (DE); Ernst Roemer, Dorsten (DE); Peter Reinemer, Munich (DE); Kathrin Reinhardt, Dortmund (DE); Annie George, Puchong (MY); Nur Hanisah Mohtar, Skudai (MY); Noorsyarida Mohd Sapiai, Ipoh (MY)

(73) Assignee: Biotropics Malaysia Berhad, Kuala Lumpur (MY)

( * ) Notice: Subject to any disclaimer, the term of this patent is extended or adjusted under 35 U.S.C. 154(b) by 148 days.

(21) Appl. No.: 13/402,675

(22) Filed: Feb. 22, 2012

(65) Prior Publication Data

US 2012/0245113 A1 Sep. 27, 2012

Related U.S. Application Data

(60) Provisional application No. 61/467,096, filed on Mar. 24, 2011.

(51) Int. Cl.
| | |
|---|---|
| *A61K 31/70* | (2006.01) |
| *A61K 31/34* | (2006.01) |
| *C07D 407/08* | (2006.01) |
| *C07D 407/04* | (2006.01) |
| *C07H 17/08* | (2006.01) |

(52) U.S. Cl.
CPC ............ *C07D 407/08* (2013.01); *C07D 407/04* (2013.01); *C07H 17/08* (2013.01)
USPC ................................ 514/27; 514/32; 514/468

(58) Field of Classification Search
None
See application file for complete search history.

(56) References Cited

PUBLICATIONS

R. J. Griffiths et al. "Leukotriene B4 plays a critical role in the progression of collagen-induced arthritis" Proc. Natl. Acad. Sci. USA vol. 92, Jan. 1995; pp. 517-521.
Iversen L, Kragballe K, Ziboh VA; "Significance of Leukotriene-A4 Hydrolase in the Pathogenesis of Psoriasis" Skin Pharmacol 1997;vol. 10; pp. 169-177.
K. C. Nicolaou et al. "The Art and Science of Total Synthesis at the Dawn of the Twenty-First Century" Angew. Chem. Int. Ed. 2000, vol. 39, pp. 44-122.
Eisei Noiri et al. "An in vivo approach showing the chemotactic activity of leukotriene B4 in acute renal ischemic-reperfusion injury" Proceddings of the National Academy of Sciences of the Jan. 18, 2000; vol. 97; pp. 823-828.
P. Sharon and W. Stenson "Enhanced synthesis of leukotriene B4 by colonic mucosa in inflammatory bowel disease" Gastroenterology. Mar. 1984;vol. 86(3):pp. 453-460.
A.M. Tagera and A.D. Luste "Prostaglandins, Leukotrienes and Essential Fatty Acids: BLT1 and BLT2: the leukotriene B4receptors" vol. 69, Issues 2-3, Aug.-Sep. 2003, pp. 123-134.
C. Turner et al. "In Vitro and in Vivo Effects of Leukotriene B4 Antagonism in a Primate Model of Asthma" J Clin Invest. Jan. 15, 1996; vol. 97(2): pp. 381-387.
C. Winter et al. "Carrageenin-induced edema in hind paw of the rat as an assay for antiiflammatory drugs" Proc Soc Exp Biol Med. Dec. 1962; vol. 111:pp. 544-547.
Takehiko Yokomizo et al. "A Second Leukotriene B4 Receptor, BLT2: A New Therapeutic Target in Inflammation and Immunological Disorders" J Exp Med. Aug. 7, 2000; vol. 192(3): pp. 421-431.
Iain B. McInnes "Leukotrienes, mast cells, and T cells" 2003 Arthritis Res. Ther. vol. 5 pp. 288-289,2003.
P.M. Giles, Jr. "Revised Section F: Natural Products and Related Compounds" Pure Appl. Chem., vol. 71, No. 4, pp. 587-643, 1999.
Claudia R. Turner et al. "In Vitro and in Vivo Effects of Leukotriene B4 Antagonism in a Primate Model of Asthma" vol. 97, No. 2, Jan. 1996, pp. 381-387.
Iversen et al, "Significance of leukotriene-A4 hydrolase in the pathogenesis of psoriasis" Skin. Pharmacol.1997, vol. 10, Abstact.
P. Sharon et al. "Enhanced synthesis of leukotriene B4 by colonic mucosa in inflammatory bowel disease" vol. 86, Issue 3 , Abstact, Mar. 1984.

*Primary Examiner* — Traviss C McIntosh, III
(74) *Attorney, Agent, or Firm* — Maschoff Brennan

(57) ABSTRACT

The use or methods of use of extracts comprising one or more special clerodane compounds against inflammatory (including allergic) diseases or conditions, as well as novel compounds of this type, said clerodane derivatives for use against inflammatory (including allergic) diseases or conditions, pharmaceutical formulations comprising them especially for use against inflammatory disease or conditions, and related embodiments; said extract and/or compound(s) for use in the treatment or in the preparation of a medicament (including a nutraceutical) for the prophylactic and/or therapeutic treatment of said disease or condition, as well as their preparation; pharmaceutical or nutraceutical formulations comprising said extract and/or natural compound(s) which are useful in said prophylactic and/or therapeutic treatment, and related embodiments.

7 Claims, 4 Drawing Sheets

CLERODANE DERIVATIVES FOR MODULATION OF LEUKOTRIENE RECEPTOR ACTIVITY AND RELATED DISEASES

RELATED APPLICATION

This application claims the benefit of U.S. Provisional Application No. 61/467,096, filed Mar. 24, 2011, which is incorporated herein by reference.

SUMMARY OF THE INVENTION

The invention relates to the use or methods of use of extracts comprising one or more special clerodane compounds against inflammatory (including allergic) diseases or conditions, as well as novel compounds of this type, said clerodane derivatives for use against inflammatory diseases or conditions, pharmaceutical formulations comprising them especially for use against inflammatory disease or conditions, and related embodiments. The invention relates also to said extract and/or compound(s) for use in the treatment or in the preparation of a medicament (including a nutraceutical) for the prophylactic and/or therapeutic treatment of said disease or condition, as well as their preparation. It also relates to pharmaceutical or nutraceutical formulations comprising said extract and/or natural compound(s) which are useful in said prophylactic and/or therapeutic treatment. They can also be used for non-therapeutic, e.g. cosmetic, purposes only. Other invention embodiments are described below.

BACKGROUND OF THE INVENTION

Leukotriene receptor antagonists (LTRA) and inhibitors of leukotriene synthesis (5-lipoxygenase inhibitor) have become available in the last decade. These leukotriene modifiers, as a class, have been shown to be effective in the treatment of chronic asthma and exercise-induced bronchio-constriction. Currently, the LTRAs are recommended as first-line preventer agents and second-line controller agents in the treatment of chronic asthma. McInnes (Arthritis Res Therapy 5(6): 288-9, 2003) published that "LTB4 antagonists are effective in reducing collagen- and cytokine-induced arthritis, and 5-LO-deficient mice exhibit reduced collagen-induced arthritis." While Hicks et al stated in 2007 "Leukotriene B(4) (LTB(4)) is a lipid inflammatory mediator derived from membrane phospholipids by the sequential actions of cytosolic phospholipase A2 (PLA2), 5-lipoxygenase (5-LO) and leukotriene A(4) (LTA(4)) hydrolase. Several inflammatory diseases, including asthma, chronic obstructive pulmonary disease, arthritis and inflammatory bowel disease, have been associated with elevated levels of LTB(4). As a result, pharmacological strategies to modulate the synthesis of LTB (4) (inhibition of PLA2, 5-LO or LTA(4) hydrolase) or the effects of LTB(4) itself (antagonism of LTB(4) receptors) are being developed by several companies. Two G-protein-coupled receptors mediate the effects of LTB(4), namely BLT1 and BLT2. The pharmacology, expression and function of these two receptors were last reviewed by Tager and Luster in 2004. Since then, there has been an increased understanding of the function of these receptors, in particular for BLT2, the less well understood of the two receptors. Furthermore, since the last review in 1996, there have been several clinical developments in the use of BLT receptor antagonists for inflammatory diseases.

Pfizer was developing CP-195543, a leukotriene B4 (LTB4) antagonist, for the potential treatment of inflammatory conditions. In June 2006, the compound entered a phase II trial for rheumatoid arthritis (RA)

Singulaire (Montelukast®, trademark by Merck & Co) is a leukotriene receptor antagonist (LTRA) used for the maintenance treatment of asthma and to relieve symptoms of seasonal allergies. It is usually administered orally. Montelukast blocks the action of leukotriene D4 on the cysteinyl leukotriene receptor CysLT1 in the lungs and bronchial tubes by binding to it. This reduces the bronchoconstriction otherwise caused by the leukotriene, and results in less inflammation.

Most diterpenoids are cyclic; two types are presented in the scheme below. The numbering of the atoms is according to the IUPAC rules (Pure Appl Chem, 71(4): 587-643, 1999; Section F). In nature the labdane type is widespread whereas the clerodane type is rather rare. Within the latter group often the methyl group (carbon 19) is lost in biosynthesis, resulting in so called nor-clerodanes.

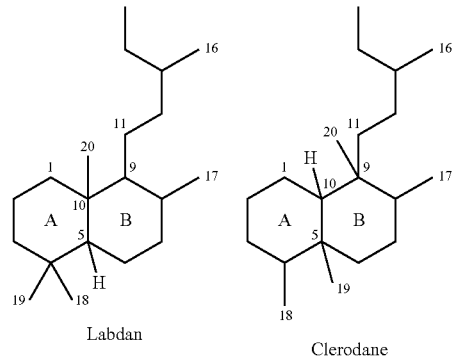

scheme A

Labdan     Clerodane

The compounds of the invention represent a subgroup of clerodanes including the one in scheme (B), the acids at the positions 17 and 18 might form lactones with the hydroxy groups at the positions 12 and/or 6. In some cases it is possible that the double bond in ring A is hydroxylated and further derivatised as the other hydroxyl groups in positions 12 and 6 which all might be substituted preferably with a carbohydrate group as defined below. The compounds of the invention are further characterized by a saturated ring B.

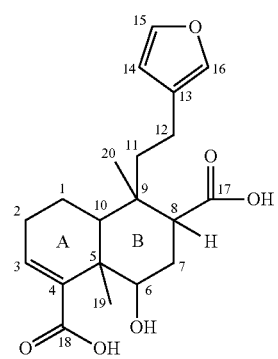

scheme B

Leukotriene B4 (LTB4; 5[S],12[R]-dihydroxy-6,14-cis-8,10-trans-eicosatetraenoic acid) is a metabolite of arachidonic acid and is one of the most potent activators of granulocytes and macrophages. LTB4 binds to a specific G protein-coupled receptor (GPCR) named BLT (also called LTB4 receptor hereinafter) and activates the Gi and G16 classes of G proteins to inhibit adenylyl cyclase and activate phospholipase C. Exposure to LTB4 induces adhesion of granulocytes to endothelial cells, degranulation of the lysosomal enzymes, generation of superoxide, and transmigration of granulocytes, all important in the host defense against foreign organisms.

Overproduction of LTB 4 is involved in inflammatory diseases including psoriasis (Iversen, Skin. Pharmacol., 10:169-77, 1997), bronchial asthma (Turner, Clin. Invest. 97:381-387, 1996), rheumatoid arthritis (Griffith, Proc. Natl. Acad. Sci. USA. 92:517-521, 1995), inflammatory bowel diseases (Sharon, Gastroenterology. 86:453-460, 1984), and ischemic renal failure (Noiri, Proc. Natl. Acad. Sci. USA. 97:823-828, 2000).

Inflammation induced by carrageenan, originally described by Winter (Proc. Soc. Exp Biol Med 111: 544-7, 1962), is acute, nonimmune, well-researched, and highly reproducible. Cardinal signs of inflammation—edema, hyperalgesia, and erythema—develop immediately following subcutaneous injection, resulting from action of proinflammatory agents—bradykinin, histamine, tachykinins, complement and reactive oxygen, and nitrogen species. Such agents can be generated in situ at the site of insult or by infiltrating cells. Neutrophils readily migrate to sites of inflammation and can generate proinflammatory reactive oxygen and other species. The inflammatory response is usually quantified by increase in paw size (edema) which is maximal around 5 h postcarrageenan injection and is modulated by inhibitors of specific molecules within the inflammatory cascade.

GENERAL DESCRIPTION OF THE INVENTION

Surprisingly, it has now been found that a certain class of compounds, namely certain clerodane compounds and derivatives thereof, that can be obtained from *Tinospora* species, have the property to modulate, especially inhibit, binding of LTB4 to its receptor. They are thus useful in the treatment of diseases, disorders or conditions that respond to such modulation.

Surprisingly, the compounds of the invention or useful according to the invention can be isolated from *Tinospora crispa* (Malaysian Pharmacopeia) whereas related species as *Tinospora cordifolia* (Indian Pharmacopeia) produce compounds with a different carbon skeleton (nor-clerodanes, e.g. nor-19 methyl clerodanes) and *T. capillipes*, *T. sagittata* produce compounds where ring B in scheme B shown above is non oxygenated at position 6.

More surprising some new compounds of this type of secondary metabolites can be isolated from *T. crispa*. These are mainly characterized by the non derivatised carbonic acid at carbon 17 in scheme B above.

DETAILED DESCRIPTION OF THE INVENTION

In a first embodiment, the invention relates to a compound of the formula I, or an extract comprising a compound of the formula I,

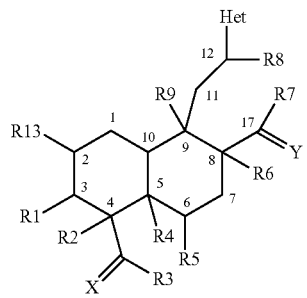

(without numbering of the carbons formula I*:

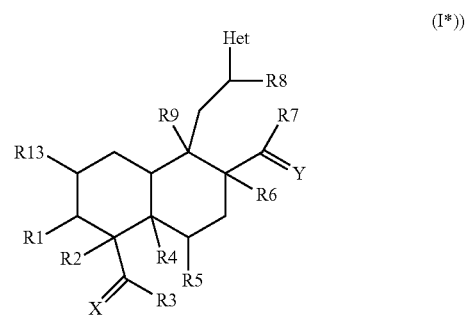

wherein
R1 is OR10 wherein R10 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
R2 is hydrogen, hydroxy, or etherified or esterified hydroxy, e.g. $C_1$-$C_8$-alkoxy, $C_1$-$C_8$-alkanoyloxy or benzoyloxy;
or R1 and R2 together form a double bond;
R3 is hydroxy or etherified or esterified hydroxy, e.g. $C_1$-$C_8$-alkoxy, $C_1$-$C_8$-alkanoyloxy or benzoyloxy;
R4 is $C_1$-$C_8$-alkyl, especially methyl;
R5 is hydroxy or etherified or esterified hydroxy, e.g. OR11 wherein R11 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
or R3 and R5 together with their bonds form —O— or —S— (forming together with the atoms to which they are bound a lactone or thiolactone ring);
R7 is hydroxy or etherified or esterified hydroxy, e.g. $C_1$-$C_8$-alkoxy, $C_1$-$C_8$-alkanoyloxy or benzoyloxy;
or R5 and R7 together with their bonds form —O— or S_ (forming together with the atoms to which they are bound a lactone or thiolactone ring)
R6 is hydrogen, hydroxy or etherified or esterified hydroxy, e.g. $C_1$-$C_8$-alkoxy, $C_1$-$C_8$-alkanoyloxy or benzoyloxy;
R8 is OR12 wherein R12 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy0;
or R7 and R8 together with their bonds form —O— or —S— (forming together with the atoms to which they are bound a lactone or thiolactone ring);
R9 is $C_1$-$C_8$-alkyl, especially methyl;
R13 is hydrogen or OR14 wherein R14 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;

X is O or S;
Y is O or S;
and Het is an unsaturated, partially saturated or saturated heterocyclyl with 4 to 8 ring atoms of which 1 or two are oxygen, which heteroaryl is unsubstituted or substituted with one or more moieties independently selected from the group consisting of hydroxy, etherified or esterified hydroxyl, e.g. $C_1$-$C_8$-alkoxy, $C_1$-$C_8$-alkanoyloxy or benzoyloxy, in free form, in the form of a salt, in the form of tautomers, and/or in the form of a solvate, for USE as defined below, e.g. for use in the (prophylactic and/or therapeutic) treatment of an inflammatory disease, or condition, especially one that responds to the modulation of LTB4 receptor in a mammal;

or for use as active ingredient in a pharmaceutical, including nutraceutical, formulation for the (prophylactic and/or therapeutic) treatment of said disease or condition.

Especially preferred according to the invention is a compound of the formula I, especially I*, wherein R1 is OR10 where R10 is hydrogen or a hexose radical bound via one of its oxygen atoms;
R2 is hydroxy;
or R1 and R2 together form a double bond;
R3 is OH or O—$CH_3$;
R4 is methyl;
R5 is hydroxyl or OR11 with R11=hexose radical bound via one of its oxygen atoms or R3 and R5 together with their bonds form —O— (forming together with the atoms to which they are bound a lactone ring;
R6 is H;
R7 is OH or O—$CH_3$;
or R5 and R7 together with their bonds form —O— (forming together with the atoms to which they are bound a lactone ring;
R8 is OH or OR12 wherein R12 is hydrogen or a hexose radical bound via one of its oxygen atoms;
or R7 and R8 together with their bonds form —O— (forming together with the atoms to which they are bound a lactone ring);
R9 is methyl;
R13 is hydrogen or OR14 wherein R14 is hydrogen or a hexose radical bound via one of its oxygen atoms;
X is O;
Y is O;
and Het is furan-3-yl or 2(5H)-furanon-3-yl or 5-hydroxy-2 (5H)-furanon-3-yl, in free form, in the form of a salt, in the form of tautomers, and/or in the form of a solvate;

for USE as defined below, e.g. for use in the (prophylactic and/or therapeutic) treatment of an inflammatory disease, or condition, especially one that responds to the modulation of LTB4 receptor in a mammal;

or for use as active ingredient in a pharmaceutical, including nutraceutical, formulation for the (prophylactic and/or therapeutic) treatment of said disease or condition.

In a second embodiment, the invention relates to new derivatives of the clerodane type, or an extract comprising them, where the clerodane compound is selected from the group consisting of those represented by Compounds No. COI 1, COI 5, COI 6 and COI 8 of Table 5 given below, respectively.

In a third embodiment, the invention relates to a pharmaceutical or nutraceutical formulation, comprising at least one compound of the formula I as defined above or below, or an extract comprising it, or a pharmaceutically (including nutraceutically) acceptable salt, and/or solvate (including hydrate) thereof.

In a fourth embodiment, the invention relates to the use of at least one compound of the formula I or an extract comprising it, or a pharmaceutically acceptable salt and/or solvate (including hydrate) thereof, respectively, in the prophylactic and/or therapeutic treatment of an inflammatory disease or condition, especially one that responds to LTB4 receptor modulation.

In a fifth embodiment, the invention relates to the use of a compound of the formula I or an extract comprising it, in the preparation of a pharmaceutical (including nutraceutical) formulation for use in the prophylactic and/or therapeutic treatment of an inflammatory disease, especially one that responds to LTB4 receptor modulation, as well as a method for preparing such a formulation.

In a sixth embodiment, the invention relates to a pharmaceutical and/or nutraceutical formulation useful in the therapeutic treatment of an inflammatory disease or condition, especially one that responds to LTB4 receptor modulation.

In addition, also non-therapeutic use is possible, e.g. the USE of a compound of the formula I, or a mixture of two or more such compounds, including an extract comprising them, for the cosmetic treatment of a warm-blooded animal, especially a human, comprising administering said compound or compound mixture to said animal, especially a human, in order to achieve cosmetically advantageous results; where the compound(s) can also be used in the form of a cosmetically acceptable (corresponding especially to pharmaceutically and/or nutraceutically acceptable as defined below) salt, and/or in the form of solvates.

In another embodiment, the present invention relates to a USE as defined below, in one embodiment to a method of treatment as defined below under USE, in another embodiment to a pharmaceutical formulation for use in such treatment as defined below under USE.

Specific embodiments of the invention are also represented by the claims which are incorporated here by reference, especially the dependent claims.

The general expressions, within the present disclosure, preferably have the following meaning, where in each embodiment one, more than one or all more general expressions may, independently of each other, be replaced with the more specific definitions, thus forming preferred embodiments of the invention, respectively:

Preferably, the compounds of the formula I are natural compounds, that is, compounds that are present in and can be isolated or extracted from natural sources (especially those mentioned in detail above and below) without chemical synthesis steps (though they may also be prepared or modified by chemical synthesis, e.g. acylated or the like) and are thus present as extracts or purified components of extracts, and not derivatives only obtainable by chemical synthesis.

They can also be part of an extract which is obtainable by extracting a plant or a plant part from an appropriate plant of the genus *Tinospora*.

Further, the present clerodane compounds of the formula I comprise all stereoisomers, such as those which may exist due to asymmetric carbons on the various substituents, including enantiomeric forms and diastereomeric forms. Individual stereoisomers of the clerodane compounds of the formula I of the present invention may, for example, be substantially free of other isomers, or may be admixed, for example, as racemates or with all other, more than one other or other selected stereoisomers.

To the extent that compounds the formula I and salts thereof may exist in their tautomeric form, all such tautomeric forms are contemplated herein as part of the present invention embodiments.

Where salt-forming groups (e.g. acidic groups, such as phenolic OH groups, or basic groups, such as amino or imino groups) are present within them, the clerodane compounds of the formula I may be in the free form or in the form of salts. The term "salt(s)", as employed herein, denotes acidic and/or basic salts formed with inorganic and/or organic acids and bases. In addition, when a compound of the formula I contains both a basic moiety and an acidic moiety, "inner salts" may be formed and are included within the term "salt(s)" as used herein. Pharmaceutically (or nutraceutically) acceptable (i.e., non-toxic, physiologically acceptable) salts are preferred, although other salts are also useful, e.g., in isolation or purification steps which may be employed during preparation. Salts of compounds of the formula I may be formed, for example, by reacting a compound of the formula I with an amount of acid or base, such as an equivalent amount, in a medium such as one in which the salt precipitates or in an aqueous medium followed by lyophilization. Also ion exchangers can be used to form salts from free forms or free forms from salts of a compound of the formula I. "Free form" refers to "form without salt-forming counterions", e.g. in non-salt form.

Where the compounds of the formula I (or clerodane compounds of the formula I or the like) are mentioned in the present disclosure, this also comprised the corresponding (especially pharmaceutically acceptable) salts thereof. also where not explicitly stated.

Compounds of the formula I which contain a basic moiety may form salts with a variety of organic and inorganic acids. Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerolphosphates, hemisulfates, heptanoates, hexanoates, hydrochlorides, hydrobromides, hydroiodides, 2 hydroxyethanesul-fonates, lactates, maleates, methanesulfonates, 2-naphtalene-sulfonates, nicotinates, nitrates, oxalates, pectinates, per-sulfates, 3-phenylpropionates, phosphates, picrates, pivalates, propionates, salicylates, succinates, sulfates, sulfonates, tartrates, thiocyanates, toluenesulfonates, such as tosylates, undecanoates, and the like.

The compounds of the formula I which contain an acidic moiety (e.g. carboxyl groups) may form salts with a variety of organic and inorganic bases. Exemplary basic salts include ammonium salts, non-toxic metal salts derived from metals of groups Ia, Ib, IIa and IIb of the Periodic Table of Elements, e.g. alkali metal salts such as sodium, lithium, and potassium salts, alkaline earth metal salts such as calcium or magnesium salts, or salts with other metals, such as zinc, salts with organic bases (for example, organic amines) such as such as unsubstituted or hydroxy-substituted mono-, di- or tri-alkylamines, especially mono-, di- or tri-lower alkylamines, or quaternary ammonium compounds, for example with alkyl amines, e.g. t-butyl amine, N-methyl-N-ethylamine, diethylamine, triethylamine, mono-, bis- or tris-(2-hydroxy-lower alkyl)amines, such as mono-, bis- or tris-(2-hydroxyethyl) amine, 2-hydroxy-tert-butylamine or tris(hydroxymethyl)methylamine, N,N-di-lower alkyl-N-(hydroxy-lower alkyl) amines, such as N,N-dimethyl-N-(2-hydroxyethyl)-amine or tri-(2-hydroxyethyl)-amine, or N-methyl-D-glucamine, or quaternary ammonium salts, such as tetrabutylammonium salts, or with benzathines, dicyclohexylamines, N-methyl-D-glucamines, N-methyl-D-glucamides, or salts with amino acids such as arginine, lysine and the like. Also salts with salt-forming pharmaceutical and/or nutraceutical carrier materials are possible and encompassed by the invention.

Further, the compounds of the formula I may be in the form of their solvates, such as hydrates, of these derivatives.

"A compound of the formula I" or "compound(s) of the formula I" or the like can also refer to one or more compounds of the formula I, that is one compound or a mixture of compounds of the formula I, or to the USE of a compound of the formula I, where reference to compound(s) of the formula I always includes the compound(s) as such or in the form of a salt (especially a pharmaceutically acceptable salt), a solvate and/or a tautomer thereof. In all cases this means that either only one compound (in substantially pure form or as a direct extract or a further enriched extract) or a mixture of two or more compounds of the formula I (which mixture is preferred) can be present, e.g. in an extract or pharmaceutical/nutraceutical formulation according to the invention, or that it or they can be of/for USE according to the invention.

Etherified hydroxy is preferably phenyl- or naphthylalkoxy, e.g or (more preferably) alkoxy, such as $C_1$-$C_{10}$alkoxy, e.g. methoxy or further ethoxy, n-propoxy, isopropoxy or the like.

Esterified hydroxy is preferably alkanoyloxy or benzoyloxy in which benzoyl may be unsubstituted or substituted by one or more, e.g. up to three, substituents independently selected from the group consisting of hydroxy, $C_1$-$C_8$alkoxy, $C_1$-$C_8$alkanoyloxy, such as acetoxy, carboxy and $C_1$-$C_8$alkoxycarbonyl.

For the purpose of the invention the terms "$C_1$-$C_8$alkyl", "$C_1$-$C_8$alkoxy", or "$C_1$-$C_8$alkanoyl" especially refer to alkyl radical groups selected from n-alkyl, e.g. ethyl, n-propyl, n-butyl etc, or branched primary, secondary or tertiary alkyl radical groups as defined by IUPAC Rule A-2 (Hydrocarbons) (Nomenclature of Organic Chemistry, Sections A, B, C, D, E, F, and H, Pergamon Press, Oxford, 1979. Copyright 1979 IUPAC) in conjunction with Rule A-3 (Univalent Radicals) consisting of the assigned number of carbons.

The term "carbohydrate having 2 to 30 (preferably 5 to 12) carbon atoms bound via one of its oxygen atoms" especially refers to mono. oligo- or polysaccharidyl moieties bound via one of their oxygen atoms. The carbohydrates forming the basis for such moieties include, but are not limited to, monosaccharides, disaccharides, further oligosaccharides, or polysaccharides. Monosaccharide for example includes, but is not limited to, aldotrioses such as glyceraldehyde, ketotrioses such as dihydroxyacetone, aldotetroses such as erythrose and threose, ketotetroses such as erythrulose, aldopentoses such as arabinose, lyxose, ribose and xylose, ketopentoses such as ribulose and xylulose; hexoses, especially aldohexoses such as allose, altrose, galactose, glucose, gulose, idose, mannose and talose or, ketohexoses such as fructose, psicose, sorbose and tagatose; heptoses such as mannoheptulose, sedoheptulose, octoses such as octolose, 2-keto-3-deoxy-manno-octonate, nonoses such as sialoseallose. Disaccharides for example include, but are not limited to, glucorhamnose, trehalose, sucrose, lactose, maltose, galactosucrose, N-acetyllactosamine, cellobiose, gentiobiose, isomaltose, melibiose, primeverose, hesperodinose, and rutinose. Oligosaccharides for example include, but are not limited to, raffinose, nystose, panose, cellotriose, maltotriose, maltotetraose, xylobiose, galactotetraose, isopanose, cyclodextrin (.alpha.-CD) or cyclomaltohexaose, .beta.-cyclodextrin (.beta.-CD) or cyclomaltoheptaose and .gamma.-cyclodextrin (.gamma.-CD) or cyclomaltooctaose. Polysaccharides for example include, but are not limited to, xylan, mannan, galactan, glucan, arabinan, pustulan, gellan, guaran, xanthan, and hyaluronan. Some examples include, but not limited to, starch, glycogen, cellulose, inulin, chitin, amylose and amylopectin.

In the case of di-, oligo- and polysaccharides, the bonds between the carbohydrate subunits may include various possible types, e.g. preferably in the form of glycosidic connections of the 1→4 and 1→6 types.

Especially preferred is a mono- or disaccharide carbohydrate moiety (preferably with 5 to 12 carbon atoms) bound via one of its oxygen atoms, especially selected from the glucosidyl (D-Glucohexapyranosidyl) and the Gentioniosidyl moiety (beta (1->6) di-glucosidyl or 6-=-beta-D-glucohexapyranosyl-D-glucosidyl).

The carbohydrates may carry one, more or all hydroxyl groups in modified form, e.g. as etherified hydroxyl or especially esterified hydroxyl as defined above, respectively, for example in acetylated, e.g. per-acetylated, form.

Preferably, the total weight share (concentration) of the compound or all compounds of the formula I in an extract or mixture of compounds of the formula I or a purified compound of the formula I that is of USE according to the invention in the final extract, mixture or compound (direct or further enriched) is in the range from 0.01 to 100% by weight, more preferably from 1 to 100 or to 99% by weight, in another embodiment from 5 to 100 or to 99% by weight, or from 20 to 100 or to 95% by weight, or e.g. from 50 to 100 or to 90% by weight.

Where relative amounts of components are given in %, this means weight %, if not indicated otherwise.

"Obtainable" means that a product (e.g. extract or compound) may be obtained by the specified or other methods, or preferably it is obtained by the specified method.

As used herein, the term "therapeutical treatment" or "therapeutically effective amount" means the kind or amount of the active compound(s) of the formula I in the composition that will elicit the biological or medical response in a tissue, system, subject, or human that is being sought e.g. by the researcher, veterinarian, medical doctor or other clinician, which includes alleviation of the symptoms of the disease or condition being treated up to and including complete cure. The novel methods of treatment of this invention are for disorders (diseases or conditions) known to those skilled in the art.

As used herein, the term "prophylactic treatment" or "prophylactically effective amount" means the kind or amount of the active compound(s) of the formula I in the composition that will elicit the biological or medical response in a tissue, system, subject, or human that is being sought e.g. by the researcher, veterinarian, medical doctor or other clinician, to prevent the onset of a disorder, disease or condition in subjects at risk for a disorder, disease or condition as mentioned herein.

Where solely "treatment" is used, this refers to prophylactic and/or therapeutic treatment, or any one thereof.

For testing, it is possible to conduct clinical trials (or animal assays as described in the Examples). e.g. clinical trials with humans (or other animals)

The extracts or compound(s) of the formula I as such or of USE according to the invention may be used as such, in the form or pharmaceutical or nutraceutical formulations (the latter term including food additives=supplements) or in the form of functional food.

Where a compound or mixture of compounds of the formula I are used as supplement, this means that the compound(s), extracts or a pharmaceutical or nutraceutical formulation comprising them, each according to the invention, can be added to any other nutrient or pharmaceutical or nutraceutical. Thus they can especially serve as food supplement. However, the compound(s) or formulations may also be administered as such.

The activity against LTB4 receptor or inflammatory diseases or disorders can, for example, be tested as described in the Examples, especially in the in vivo experiments e.g. with mice, rats or rabbits described there.

The so called, rat paw edema assay is a classic assay used to assess the ability of a putative anti-inflammatory agent to prevent the edema that would otherwise have been produced by the injection of a pro-inflammatory agent (Winter et. al., Proc. Soc. Exp. Biol. Med. 111, 544 (1962)).

"Nutraceuticals", "Functional Food", or "Functional Food products" (sometimes also called "Foodsceuticals", "Medicinal Food" or "Designer Food") for USE according to the present invention are defined as food products (including beverages) suitable for human consumption—the expression comprises any fresh or processed food having a health-promoting and/or disease-preventing property beyond the basic nutritional function of supplying nutrients, including food made from functional food ingredients or fortified with health-promoting additives, especially with effects in the prophylaxis or treatment of an inflammatory disease or condition, especially one that responds to LTB4 receptor modulation, and in which a compound or an extract comprising such compound(s) or a compound mixture of compounds of formula I, respectively, according to the invention is used as an ingredient (especially additive) as health benefit agent, especially in an effective amount.

"Comprising" or "including" or "having" wherever used herein is meant not to be limiting to any elements stated subsequently to such term but rather to encompass one or more further elements not specifically mentioned with or without functional importance, that is, the listed steps, elements or options need not be exhaustive. In contrast, "containing" will be used where the elements are limited to those specifically after "containing".

Where "about" is used or a specific numerical value is given without explicitly mentioning "about", this preferably means that a given value may deviate to a certain extent from the value given, e.g. in one of the invention embodiments by ±20% of the given numerical value, in another embodiment by ±10%. Also where "about" is not mentioned, this is implicitly to be considered present, in other invention embodiments as absent.

The term "compound mixtures" includes especially extracts comprising mixtures of two or more compounds of the formula I, where extracts are not mentioned separately.

The term "an inflammatory disease or condition" includes inflammatory diseases or conditions of any (e.g. acute or chronic), including autoimmune disease related inflammation, inflammation associated with the pathophysiological condition of other diseases or substances (e.g. infection, cancer, drugs or the like), allergy, and the like, especially where said disease or condition is selected from the following:

A disorder or condition a) of the airways, including, rhinitis, chronic bronchitis, adult/acute respiratory distress syndrome (ARDS), or dyspnea associated therewith;

b) of the eye, including conjunctivitis, ceratoconjunctivitis, uveitis, other eye inflammation;

c) of skin, including psoriasis, insect bite related inflammatory responses, sunburn related inflammatory responses, dermatitis, e.g. atopic dermatitis, lupus erythematosus;

d) of the gastrointestinal tract, immune disorders of the gut (e.g., celiac disease), bowel irregularity, including irritable bowel syndrome (IBS), or inflammatory bowel disease (IBD), including, e.g., ulcerative colitis, Crohn's disease, (Morbus Crohn), Morbus Behçet, and short bowel syndrome;

e) of the bone, muscle or joints, including Morbus Bechterev, myositis, such as polymyositis, rheumatoid arthritis, osteoarthritis, or inflammation related bone loss;

f) of other organs or tissues e.g. inflammatory diseases of the genitourinary tract, e.g. bladder inflammation, cystitis, e.g. interstitial cystitis, or nephritis, e.g. ischemic renal failure, prostatitis, e.g. chronic non-bacterial prostitis, ovaritis, or otitis;

g) allergy of various type, e.g. allergy related gastrointestinal diseases, skin allergy, allergic conjunctivitis or allergic rhinitis;

or any combination of two or more such diseases or conditions.

Especially, the treatment includes preventing the synthesis, the action, or the release of leukotrienes in a mammal.

Throughout the present specification, the prophylactic and/or therapeutic treatment or regulation of inflammatory and allergic conditions which are influenced by the formation and/or activity of leukotriene B4 are especially preferred embodiments according to the present invention.

The functional food products or pharmaceutical products according to the invention may be manufactured according to any suitable process, preferably comprising extraction of one or more compounds of the formula I and admixing to a functional food product or at least one nutraceutically or pharmaceutically acceptable carrier.

A functional food or a pharmaceutical or nutraceutical formulation comprising a compound, more preferably a compound mixture, for USE according to the present invention, can, for example, be obtained by (a) extraction of one or more compounds and/or mixture of compounds of the formula I from plants or plant parts, especially roots, from *Tinospora* spp., especially *Tinospora crispa*, more especially crawling roots, preferably in comminuted, e.g. chopped or ground/milled or crushed (e.g. in particle or powder) form by means of a hydrophilic (preferably aqueous) solvent or solvent mixture; and, if desired, (b) mixing the resulting extract comprising one or more compounds and/or mixtures of compounds of the formula I as active ingredient in the preparation of the functional food product with the other constituents thereof or in order to obtain a pharmaceutical or nutraceutical formulation with one or more carrier materials or with a solvent or dispersant (allowing to form a suspension or emulsion).

Further processing steps may precede and/or follow, such as drying (e.g. freeze-drying, spray-drying, fluid bed or spouted bed or other evaporation drying), granulation, agglomeration, concentrating (e.g. to syrups, formed via concentration and/or with the aid of thickeners), pasteurizing, sterilizing, freezing, dissolving, dispersing, filtering, centrifuging, confectioning, and the like.

When one or more compounds and/or a compound mixture according to the invention are added to a food product or pharmaceutical or nutraceutical, this also results in a functional food product or pharmaceutical or nutraceutical formulation according to the invention.

Preferably, a functional food product (nutraceutical) according to the invention (which is different from the corresponding plant itself) comprises 0.001 to 30, e.g. 0.002 to 20, such as preferably 0.01 to 5, weight-% (concentration) of a compound or mixture of compounds of the formula I according to the invention, the rest being food and/or nutraceutically acceptable carriers and optionally customary additives.

Further additives may be included, such as vitamins, minerals, e.g. in the form of mineral salts, unsaturated fatty acids or oils or fats comprising them, other extracts, or the like.

The functional food products according to the invention may be of any food type. They may comprise one or more common food ingredients in addition to the food product, such as flavours, fragrances, sugars, fruit, minerals, vitamins, stabilizers, thickeners, dietary fibers, protein, amino acids or the like in appropriate amounts, or mixtures of two or more thereof, in accordance with the desired type of food product.

Examples of basic food products and thus of functional food products according to the invention are fruit or juice products, such as orange and grapefruit, tropical fruits, banana, apple, peach, blackberry, cranberry, plum, prune, apricot, cherry, peer, strawberry, marionberry, black currant, red currant, tomato, vegetable, e.g. carrot, or blueberry juice, soy-based beverages, or concentrates thereof, respectively; lemonades; extracts, e.g. coffee, tea, green tea; dairy type products, such as milk, dairy spreads, quark, cheese, cream cheese, custards, puddings, mousses, milk type drinks and yoghurt; frozen confectionary products, such as ice-cream, frozen yoghurt, sorbet, ice milk, frozen custard, water-ices, granitas and frozen fruit purees; baked goods, such as bread, cakes, biscuits, cookies or crackers; spreads, e.g. margarine, butter, peanut butter honey; snacks, e.g. chocolate bars, muesli bars; pasta products or other cereal products, such as muesli; ready-to-serve-dishes; frozen food; tinned food; syrups; oils, such as salad oil; sauces, such as salad dressings, mayonnaise; fillings; dips; chewing gums; sherbet; spices; cooking salt; instant drink powders, such as instant coffee, instant tee or instant cocoa powder; instant powders e.g. for pudding or other desserts; meat fish or fish or meat products, such as sausages, burgers, meat loafs, meatballs, meat extracts, canned or tinned fish or meat, meat vol-au-vent, meat or fish soup, meat or fish skewers, fish fingers; or the like.

One or more other customary additives may be present, such as flavour, fragrances or other additives, such as one or more selected from stabilizers, e.g. thickeners; colouring agents, such as edible pigments or food dyes; bulking agents, such as fruit pulp, e.g. in dried form; polyols, such as xylitol, mannitol, maltitol or the like; preservatives, such as sodium or potassium benzoate, sodium or calcium carbonate or other food grade preservatives; antioxidants, such as ascorbic acid, carotionoids, tocopherols or polyphenols; mono-, oligo- or polysaccharides, such as glucose, fructose, sucrose, soy-oligosaccharides, xylo-oligosaccharides, galacto-oligosaccharides; other artificial or natural non- or low-caloric sweeteners, such as aspartame or acesulfame; bitterness blockers; acidifiers in the form of edible acids, such as citric acids, acetic acid, lactic acid, adipic acid; flavours, e.g. artificial or natural (e.g. botanical flavours); emulsifiers; thiols, e.g. allylic thiols; diluents, e.g. maltodextrose; wetting agents, e.g. glycerol; stabilizers; coatings; isotonic agents; absorption promoting or delaying agents; and/or the like.

The one or more compounds of the formula I or compound mixtures thereof according to the invention can also be comprised in confectioned formulations to be added to foods including beverages, e.g. in the form of powders or granules, e.g. freeze-dried or spray-dried, concentrates, solutions, dispersions or other instant form, or the like.

Preferably, a pharmaceutical formulation (or also a nutraceutical in the form of a food supplement) according to the invention (which is different from the corresponding plant itself) comprises 0.001 to 100, e.g. 5 to 99, such as preferably 10 to 98, weight-% (concentration) of a compound or mixture of compounds of the formula I according to the invention, the rest being pharmaceutically and/or nutraceutically acceptable carriers and optionally other customary additives.

The pharmaceutical or nutraceutical formulation(s) (=composition(s), also for non-therapeutic, e.g. cosmetic, use) according to the present invention can be for enteral, parenteral, topical or any other route of administration, especially enteral, e.g. anal, nasal or especially oral, and can be prepared in various forms, such as granules, tablets, pills, syrups, solutions, dispersions, suppositories, capsules, suspensions, salves, lotions and the like.

Pharmaceutical grade or nutraceutical grade organic or inorganic carriers (pharmaceutically or nutraceutically acceptable carriers or carrier materials) and/or diluents suitable for oral and topical use can be used to formulate compositions containing the therapeutically-active compounds. Diluents known in the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The compositions may also include one or more of the following: carrier proteins such as serum albumin; buffers; fillers such as microcrystalline cellulose, lactose, corn and other starches; binding agents; sweeteners and other flavouring or fragrancing agents; colouring agents; and polyethylene glycol. Those additives are well known in the art, and are used in a variety of formulations.

For topical administration to the skin, the compositions with the lipophilic extract from *Tinospora crispa* are preferably provided as ointments, tinctures, creams, gels. solution, lotions; sprays; aerosols, dry powders, suspensions, shampoos, hair soaps, perfumes or the like.

In fact, any conventional topic composition can be utilized in this invention. Among the preferred compositions comprising the extract used according to the invention are those in the form of an ointment, gel, cream or lotion.

For example, a cosmetic composition for topical administration to the skin can be prepared by mixing the aforementioned extract with non-toxic, therapeutically inert, solid or liquid carriers customarily used in such preparations. These preparations preferably comprise 0.01 to 99 percent by weight, especially 0.02 to 50.0 percent by weight, preferably 0.05 to 10 percent by weight, e.g. 0.05 to 2 percent by weight of the extract, based on the total weight of the composition.

In preparing the topical compositions described above, customary additives such as preservatives, thickeners, perfumes and the like used in the art of cosmetic compounding of topical preparation can be used. Cream-base cosmetic compositions containing the active agent, used in accordance with this invention, can be composed of aqueous emulsions containing a fatty acid alcohol, semi-solid petroleum hydrocarbon, ethylene glycol and an emulsifying agent.

By "administered" herein is meant administration of a prophylactically and/or therapeutically effective dose of a compound of the formula I or an extract comprising compounds of the formula I or a mixture of compounds of the formula I to an animal, especially a patient. By "therapeutically effective dose" herein is meant a dose that produces the effects, for which it is administered, e.g. the prophlylactic or especially therapeutic diminuation or abolishing of one or more symptoms of a disease or condition as defined above.

Preferably, the dosage of the compound or compounds of the formula I, based on the total weight of the compound(s) of the formula I, in both nutraceutical (including use as supplement) or pharmaceutical use typically is such that the amount of the compound(s) of the formula I administered to a patient is such that it is effective in modulation of LTB4 receptor activity, especially its inhibition, or preferably a daily dose of about 0.2 to 200 g, e.g. in one invention embodiment of 0.5 to 7 g, or in another invention embodiment of 0.1 to 10 g, is administered to a person with a weight of 70 kg per day in one or more, e.g. 1 to 3, dosages (children/persons with differing weights receive a correspondingly (e.g. proportionally to the weight) modified dosage). For topical administration, the dosage may vary largely based on the area to be treated and may be as described above for 70 kg persons.

A mammal or human, especially being a "patient" or "subject" for the purposes of the present invention, includes especially humans and further other mammalian animals. Thus, the compound or extract comprising a compound of the formula I, respectively, or a mixture of compounds of the formula I, are applicable to both humans and animals. In the preferred embodiment the patient is a human. The patients will be treated either in prophylactic (e.g. in persons known to have relatives showing symptoms of a disease or condition described above or known to carry genes putting them at risk) or therapeutic intention (the latter once at least one of the symptoms of a disease or disorder mentioned above has become manifest).

Typically, the compound(s) of the formula I having therapeutic and/or prophylactic activity mentioned hereinbefore may be administered with at least one physiologically (=pharmaceutically or nutraceutically) acceptable carrier to a patient, as described herein. The total concentration of therapeutically active clerodane compound(s) of the formula I or a mixture of compounds of the formula I in the formulation may vary from about 0.001-99,999 wt %, e.g. from 0.1 to 50% by weight (concentration), the rest being the carrier material(s) and/or customary additives. Preferably, the compound or compounds of the formula I, in the embodiments of the invention, are enriched in the mixtures or extract or purified extracts, or in another embodiment as single compound, to a percentage, in independent embodiments of the invention, of up to 10, 20, 30, 40, 50, 60, 70, 75, or (meaning in (essentially) pure form) up to 80, 85, 90, 92, 94, 95, 96, 97 or 98% or more than 98% by weight (concentration) of the complete extract or purified extract, respectively.

The compound(s) of the formula I as such, within extracts or as mixture may be administered alone or in combination with other drug compounds or treatments, i.e., agents active in the prophylaxis or therapy of a disease or condition mentioned above, common diets or the like. Thus the invention also encompasses combination preparations, comprising a compound of the formula I, or a pharmaceutically acceptable salt, hydrate or other solvate thereof, and one or more other drug compounds in free or pharmaceutically acceptable salt, hydrate or other solvate form, and optionally one or more pharmaceutically or nutraceutically acceptable carrier materials.

"Combination" does not necessarily mean a fixed combination but may also mean that the compound(s) of the formula I may be administered in a chronically staggered manner with the combination partner(s), e.g. in the form of a kit of parts (which also is an embodiment of the invention) with other combination partners. Preferably, the chronically staggered administration takes place such that the combination partners mutually influence, especially intensify (e.g. by way of an additive or preferably synergistic effect) their therapeutic efficiency.

The compound(s) of the formula I, extracts comprising them or a mixture of compounds of the formula I, itself or as mixtures of certain complexity, e.g. extracts or preparations, e.g. juices etc. of the above mentioned plant or plant part extracts, of this invention are particular useful for controlling one or more symptoms of a disease or condition as defined above.

Natural compounds of the formula I, or extracts comprising one or more thereof, for USE according to the present invention are extracted and if desired purified and isolated from plants or plant parts plants or plant parts, especially roots, more especially crawling roots, from *Tinospora* spp., especially *Tinospora crispa*, preferably in comminuted, e.g. chopped or ground/milled or crushed (e.g. in particle or powder) form by means of a hydrophilic (preferably aqueous) solvent or solvent mixture.

By the term "extract", either a direct extract (in liquid or preferably dried form), e.g. obtained as described above and below, or preferably a further enriched extract (obtainable e.g. by one or more further purification steps after extraction, e.g. chromatography, e.g. preparative chromatography, for example as described below) comprising one or more, preferably two or more, compounds of the formula I is meant.

The compound(s) of the formula I in the form of an extract and extracts according to the invention can be obtained by extraction as described above or below.

Auxiliary means such as (especially ultrasonic) sonication, heating (e.g. to temperatures from room temperature to about 100° C.; e.g. the boiling point of water when it is used as extraction solvent), stirring, re-extraction, evaporation, chromatography or the like, may be used to allow for obtaining appropriate extracts.

Extraction preferably takes place with hydrophilic solvent or solvent mixture, meaning that the preferred obtainable or obtained extracts according to the invention are hydrophilic extracts.

The compound(s) of the formula I, or an extract comprising one or more of them are well soluble in aqueous organic solvents like aqueous alcohols, e.g. in ethanol. The solubility is, for example, more than 0.001, e.g. more than 0.01, or more than 0.1 mg/mL.

Examples of appropriate solvents are water or aqueous organic solvents (two or more of which can also be mixed), e.g. aqueous ketones, such as acetone, aqueous cyclic ethers, such as dioxane, and/or in a specific embodiment) aqueous alcohols, e.g. ethanol, and/or a liquid or superfluid gas, especially superfluid $CO_2$.

Preferably, the solvent may be removed after extraction, e.g. by evaporation or precipitation (e.g. by the addition of less polar solvents).

Preferably, the extracts can subsequently be further enriched by one or more additional purification steps, such as distribution, e.g. between an aqueous phase and a hydrocarbon (e.g. hexane or heptane), ether (e.g. diethyl ether), ketone (e.g. methyl isopropyl ketone) or ester (e.g. ethyl acetate or butyl acetate) phase for one or more times, precipitation (e.g. crystallisation) or especially chromatography, e.g. by HPLC or MPLC, by which it is possible to obtain further enriched extracts or isolated compounds of the formula I.

It is also possible to use other chromatographic methods such as gel permeation chromatography, countercurrent chromatography, or high speed counter current chromatography instead of the absorption chromatography described above.

Subsequent purification by preparative phase HPLC can also be carried out by the person skilled in the art using other stationary phases, such as RP8, phenyl, DIOL, C2, C4, C8 or amino.

The mobile phase mixtures may also contain additional acids (for example formic acid) or bases (e.g. ammonium hydroxide) or buffers (for example ammonium acetate).

The compound(s) of the formula I can e.g. be isolated or the extracts prepared as described in the appended examples. The method for detection can comprise high pressure liquid chromatography (HPLC) or on reversed phase silica gel (C18) with water/acetonitrile-gradient as an elution solvent with UV as well as MS detection which are used for the product analysis and production optimization. It will be clear to those having ordinary skill in this art that the compound(s) of the formula I, though per se natural products, can alternatively be synthesized according to standard methods leading to compounds identical with the natural compounds, where appropriate methods, for example, can be deduced from the following publications: March's Advanced Organic Chemistry: Reaction, Mechanisms and Structure, 5th ed. by Michael B. Smith, Jerry March, Wiley-Interscience; 2001; Classics in Total Synthesis: Targets, Strategies, Methods by K. C. Nicolaou, E. J. Sorensen John Wiley & Son Ltd, 1996 and The Art and Science of Total Synthesis at the Dawn of the Twenty-First Century. Nicolaou K C et al., Angew Chem Int Ed Engl 2000, 39 (1): 44-122.

Where USE is mentioned, this especially refers to one or more of the following embodiments of the invention which can be inserted wherever USE is mentioned:

(1) A compound of the formula I, an extract comprising a compound of the formula I or a mixture of compounds of the formula I, for use in prophylactic or therapeutic treatment of an animal, preferably a mammal, especially a human, against a disease or condition as defined above, especially that responds to LTB4 receptor modulation; e.g. simply for maintenance of a healthy body (prophylactically), or especially therapeutic treatment;

(2) A pharmaceutical or nutraceutical composition comprising a compound of the formula I, or a mixture of compounds of the formula I, as active ingredient together with a pharmaceutically or nutraceutically acceptable diluent or carrier, especially for use in the therapeutic and/or prophylactic treatment mentioned under (1).

(2') A pharmaceutical or nutraceutical composition for the treatment as mentioned under (1) comprising a compound of the formula I, or a mixture of compounds of the formula I, or especially a (preferably further enriched) extract comprising one or more compounds of the formula I, and a pharmaceutically or nutraceutically acceptable diluent or carrier, as active ingredient supplement to a food.

(3) A functional food comprising a compound of the formula I, or a mixture of compounds of the formula I, or especially a (preferably further enriched) extract, as active ingredient for the treatment as mentioned under (1).

(4) A method for the treatment as mentioned under (1) in a subject in need of such treatment, comprising administering a pharmaceutically or nutraceutically effective amount of a compound of the formula I, a mixture of compounds of the formula I, as active ingredient, to an individual ("individual" meaning a warm-blooded animal, especially a human, wherever mentioned), especially to an individual in need thereof.

(5) The use of a compound of the formula I, or a mixture of compounds of the formula I, as active ingredient for the manufacture of a medicament or nutraceutical or food supplement for the treatment mentioned under (1).

(6) A method or use as defined under (4), comprising co-administration, e.g. concomitantly or in sequence, of a therapeutically effective amount of compound of the formula I, or a mixture of compounds of the formula I, as active ingredient and a different pharmaceutically active compound and/or a pharmaceutically acceptable salt thereof, said different pharmaceutically active compound and/or salt thereof being especially for use in the treatment as mentioned under (1).

(7) A combination product comprising a therapeutically effective amount of a compound of the formula I, or a mixture of compounds of the formula I, as active ingredient, and a different pharmaceutically active compound and/or a pharmaceutically acceptable salt thereof, said second pharmaceutically active compound being especially for use or of use in the treatment mentioned under (1).

The USE may also be for purely cosmetic purposes (or generally for non-therapeutic use as defined above), wherein in all embodiments of the invention, such as the above embodiments (1) to (7), "pharmaceutical", "pharmaceutically", "nutraceutical" and "nutraceutically" are replaced with "cosmetic" or "cosmetically", respectively, thus providing the corresponding embodiments for non-therapeutic use. "Cosmetic use" in one class of embodiments of the invention refers to the use predominantly or exclusively externally on the body of the animal/human or in its oral cavity for the protection or maintenance of its good condition, for perfuming, for the modification of the external appearance or for influencing body odor, or internally for the mentioned purposes. "Cosmetic" especially refers to a non-therapeutic use, that is, a use not for treatment of a disease or condition for its cure or symptom reduction but merely to improve the aesthetic appearance of an individual.

For any of the USEs, the USE is such that the compound(s) of formula I or mixtures thereof are the active ingredient, that is, they are already alone capable of achieving the intended effect and are thus themselves the important active principle for the treatment(s) mentioned.

In any of the USEs mentioned and also as such, the compound(s) of the formula I may be present and/or administered in free form, in the form of a pharmaceutically and/or nutraceutically acceptable salt, in the form of tautomers, in the form of solvates (e.g. hydrates) and, where esterifyable groups are present; e.g. hydroxy, in the form of esters, such as lower alkanoylates, e.g. acetylates, aroylates, e.g. benzoylates, sulfonates, e.g. arylsulfonic acid esters, or the like (obtainable by reaction e.g. with the corresponding acid anhydrides, acid halogenides or by known amino acid coupling methods with coupling agents such as HATU, or the like); e.g. carboxyl, in the form of esters, such as lower alkyl, e.g. methyl or ethyl, alkaryl, e.g. benzyl, or the like (obtainable by reaction e.g. with the corresponding alcohol either after activation of the respective carboxyl group e.g. as mixed anhydride, or directly with coupling agents such as HATU, or the like).

By "administering" herein is especially meant administration of a therapeutically or nutraceutically effective dose of a compound of the formula I, or a mixture of compounds of the formula I, to a cell either in cell culture or especially to an animal, especially a human patient. By "therapeutically or nutraceutically effective dose" herein is preferably meant a dose that produces the (prophylactic or therapeutic) effects for which it is administered.

The pharmaceutical or nutraceutical preparations may be sterilized and/or may contain carrier materials or adjuvants such as preservatives, stabilizers, binders, disintegrants, wetting agents, skin or mucuous membrane penetration enhancers, emulsifiers, salts for varying the osmotic pressure and/or buffers, or other ingredients, excipients or carrier materials known in the art.

Compounds and/or mixtures of compounds of the invention can be prepared using plants or especially plant parts of *Tinospora crispa* (which designation can also comprise *Tinospora* selected from *Tinospora gibbericaulis* Hand.-Mazz., *Tinospora mastersii* Diels, *Tinospora rumphii* Boerl., *Tinospora thorelii* Gagnep., *Tinospora tuberculata* Beumee ex K. Heyne, or *Menispermum crispum* L., and for which ethnobotanical names which are often used are Patawali, Putarwali, Brotowali, Andawali, or Bo Ra Pe) or plant parts from it are the source for the extracts or compounds (including compound mixtures) according to the invention

The following examples illustrate the invention without limiting its scope.

EXAMPLES

Example 1

Crude Extract

The crawling roots of *Tinospora crispa* was collected near Bentong and Jengka, Pahang in Malaysia on 15-22 Jun. 2009. The plant material was identified and authenticated by Mr. Shamsul Khamis, Institute of Bioscience at University Putra Malaysia in Serdang, Selangor, Malaysia.

1385 g of *Tinospora crispa* crawling roots were ground into a powder using a lab mill (Retsch ZM200, Haan, Germany) and extracted twice with 4.000 ml 95% Ethanol at 40° C. using ultrasonic for 30 minutes. The resulting extract phases were combined, filtered and the organic solvent removed under reduced pressure. The remaining water phase was filled up with water to a final volume of 500 ml and subsequently extracted three times with 400 ml n-heptane and four times with 400 ml ethyl acetate by liquid/liquid separation. The n-heptane extract as well as the combined ethyl acetate extracts were dried ($Na_2SO_4$) and the solvent evaporated under reduced pressure at 50° C. The residual water phase was also evaporated under reduced pressure 50° C. The yields for the three crude extract phases are presented in Table 1.

TABLE 1

| Phases | Amount | TC No. |
| --- | --- | --- |
| n-heptane | 15000 mg | TC 1 (1) |
| ethyl acetate | 24540 mg | TC 1 (2) |
| remaining water | 61860 mg | TC 1 (3) |

Figure 1:
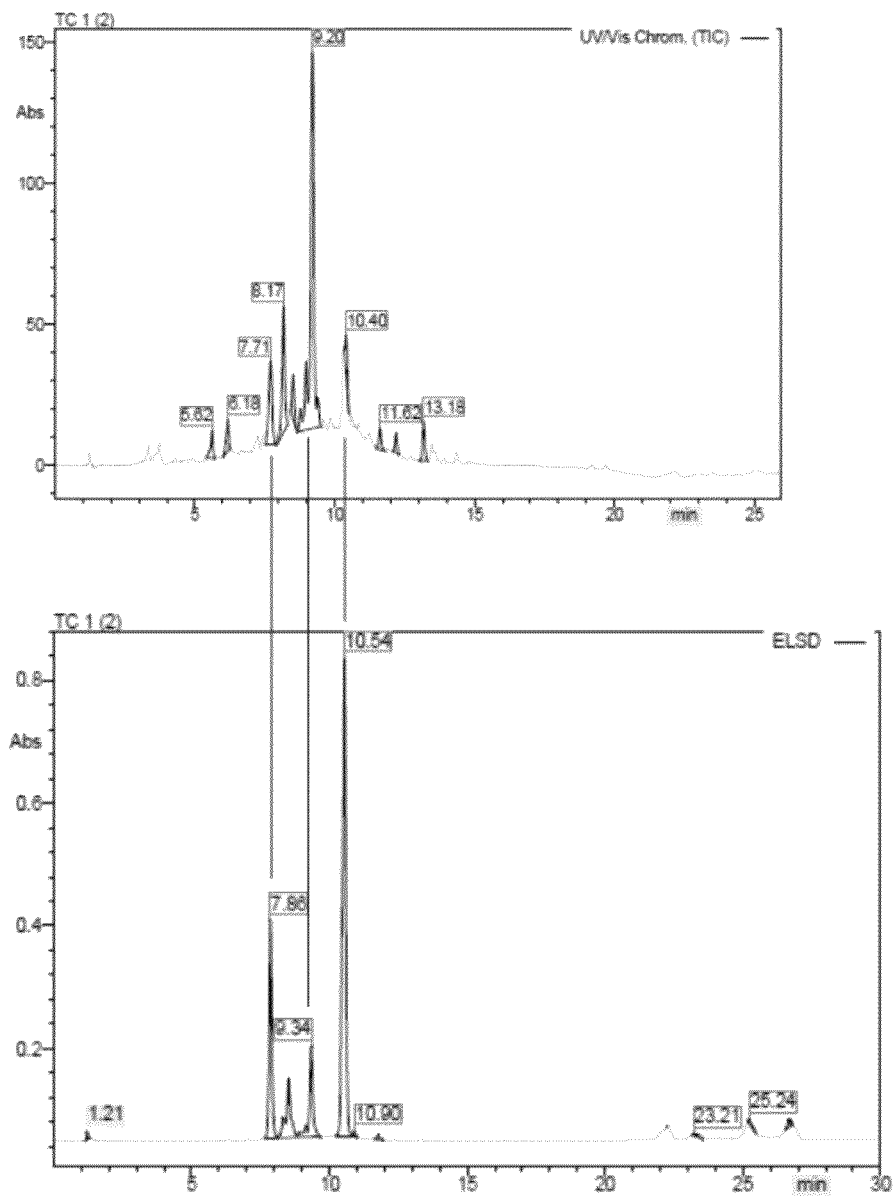
FIG. 1: Raw extract according Example 1, ethyl acetate, TC1(2), analytical method; upper line UV (Total Absorbance Current, 200-600 nm), lower line ELSD (electronic light scattering detection)
Figure 2:
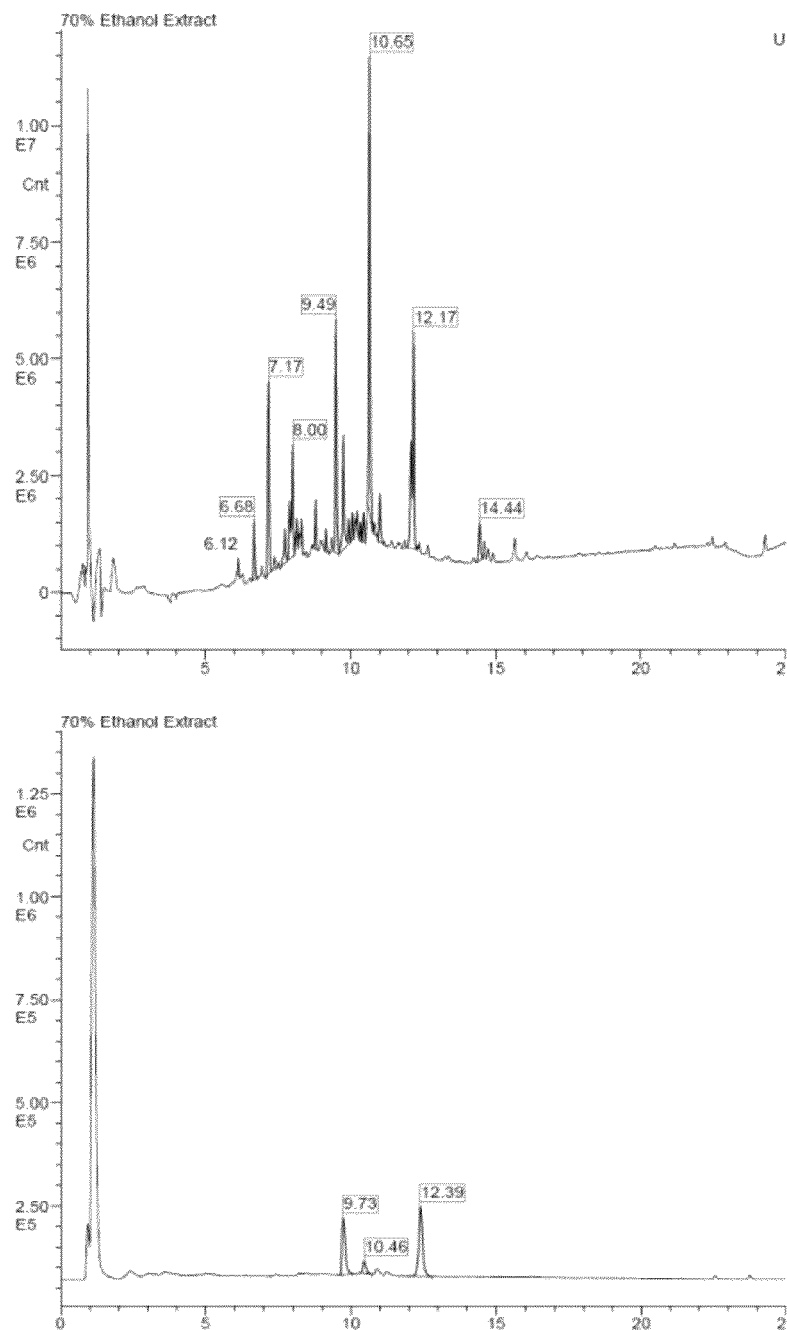
FIG. 2: HPLC of Extract 4, according Example 3, dereplication method; upper line UV (Total Absorbance Current, 200-500 nm), lower line ELSD (electronic light scattering detection)
Figure 3:
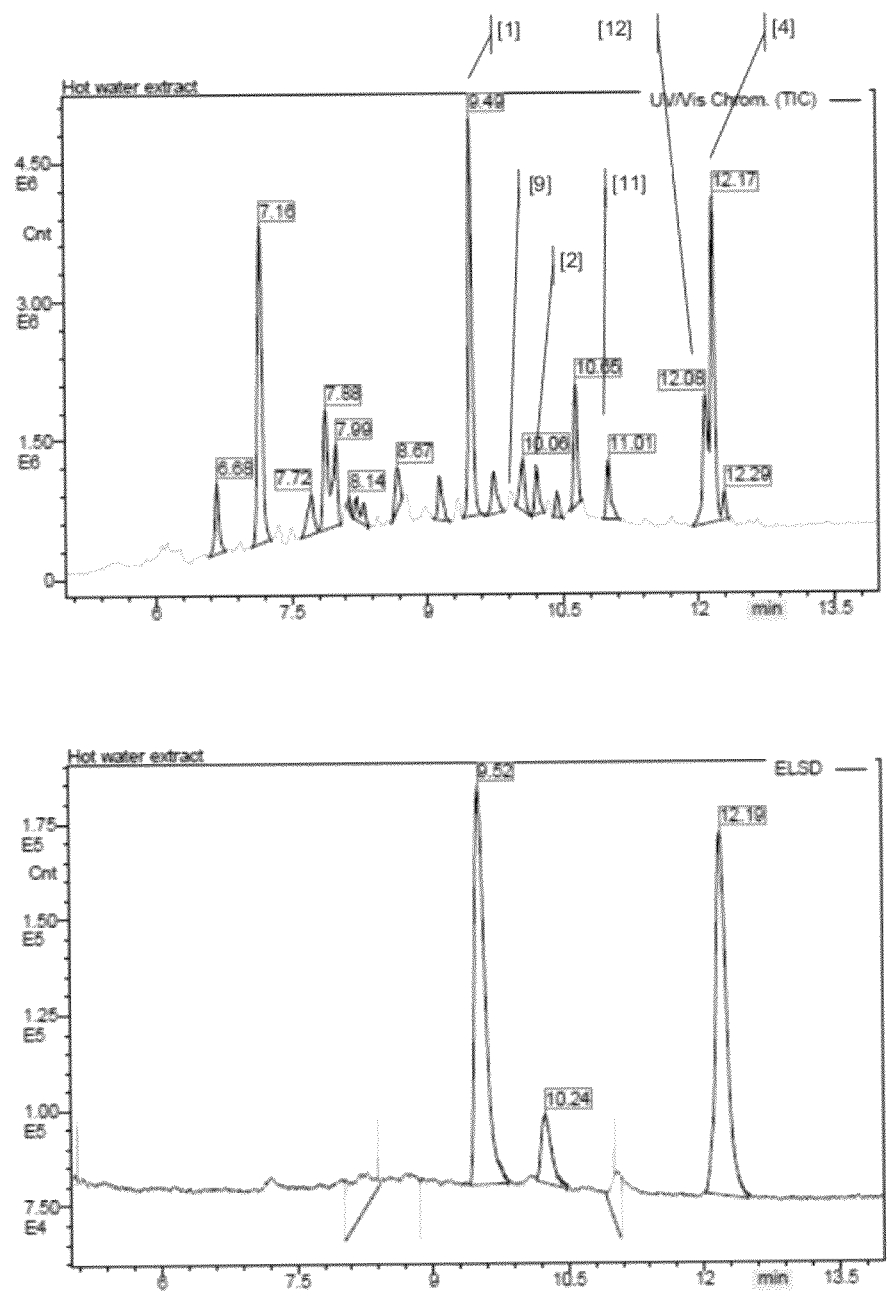
FIG. 3: HPLC of Extract 6, according Example 3, "hot water extract", dereplication method; upper line UV (Total Absorbance Current, 200-500 nm), lower line ELSD (electronic light scattering detection)
Figure 4:
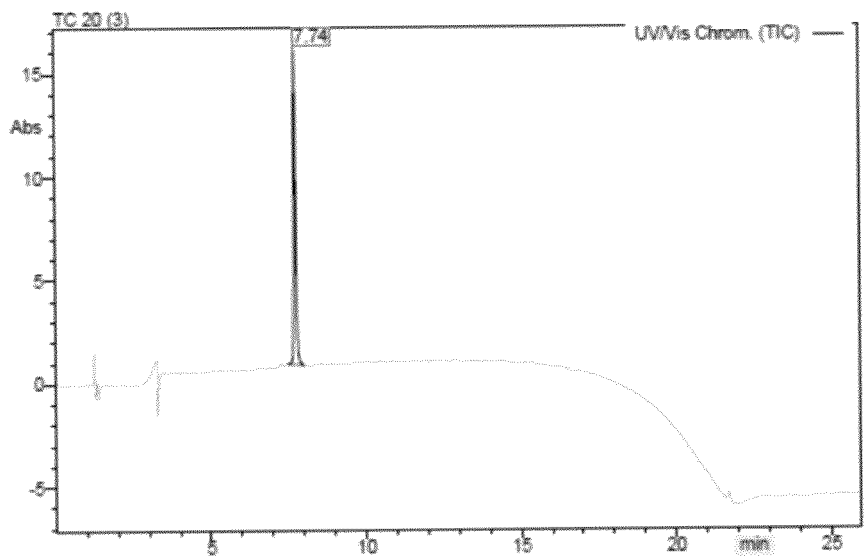
FIG. 4: HPLC of TC20, according Example 2, pure compound C014, analytic method; upper line UV (Total Absorbance Current, 200-600 nm), lower line ELSD (electronic light scattering detection)
Figure 4:
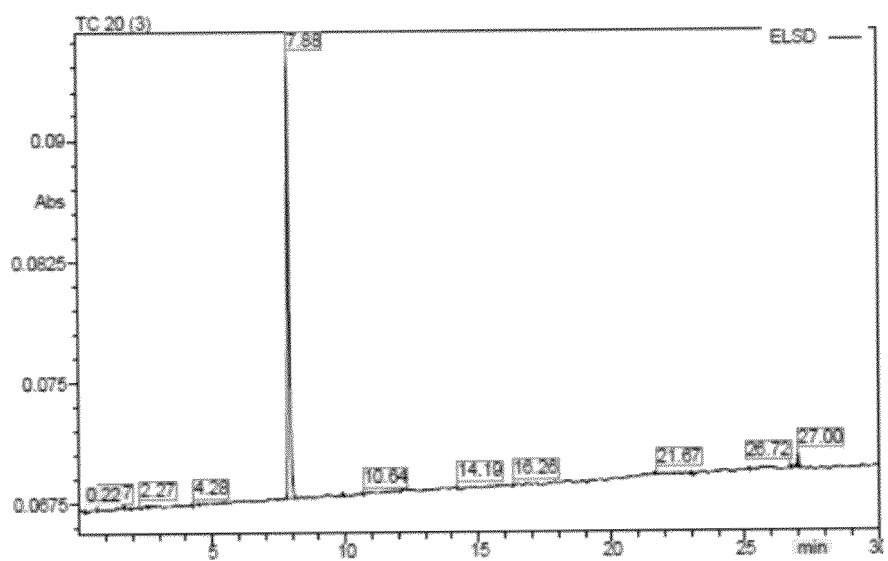

An aliquot of each extract phase was dissolved in MeOH (10 mg/ml) for analytical HPLC-UV-ELSD analysis. Only the ethyl acetate extract contains the desired compounds, e.g. Clerodane diterpenoids, and was consequently selected for further preparations. The HPLC of this extract is presented in FIG. 1.

Analytical HPLC-UV-ELSD Method:

Separations were carried out on a HP 1100 Series analytical HPLC system (Agilent, Waldbronn, Germany) comprising a G 1312A binary pump system, a G 1315A diode array detector, a G 1316A column compartment, a G 1322A degasser and a G 1313A autoinjector with a Nucleodur 100-5 C18ec column (column dimensions 125×4, Machery-Nagel, Germany), using a binary solvent system of H20+1.5% TFA (Solvent A) and acetonitrile+1.5% TFA (Solvent B). The gradient was set from 0% B to 100% B in 20 min at a flow of 1 ml/min at a column temperature of 40° C.

Example 2

Isolation of Pure Compounds

The initial separation step (procedure 1) was performed as MPLC separations on reverse phase material [on a Chromabond® (Trademark by Macherey-Nagel GmbH & Co. KG, Duren Germany) P300-20 C18 column, 370×90 mm, (Macherey & Nagel)] under following conditions (Table 2) at room temperature:

TABLE 2

"title"

| % Water | % Methanol | % 2-Propanol | Volume | Products of seperation steps |
|---|---|---|---|---|
| 80 | 20 | 0 | 1 × 2000 mL | TC 2 (1) |
| 60 | 40 | 0 | 3 × 650 mL | TC 2 (2)-TC 2 (4) |
| 40 | 60 | 0 | 5 × 400 mL | TC 2 (5)-TC 2 (9) |
| 20 | 80 | 0 | 5 × 400 mL | TC 2 (10)-TC 2 (14) |
| 0 | 100 | 0 | 5 × 400 mL | TC 2 (15)-TC 2 (19) |
| 0 | 0 | 100 | 1 × 2000 mL | TC 2 (20) |

The solvents of each fraction were evaporated under reduced pressure and analyzed by analytical HPLC-UV. For the separation of the single compounds in preparative scale a HPLC-setup was used comprising reverse phase separation columns with capacity for up to 200 mg material per separation. The gradients for elution were chosen according to the separation problem (Table 3 and Table 4). Generally the chromatographic systems were based on reverse phase and water/acetonitrile or methanol mixtures as mobile phases. Case by case the final separation step for the isolation of pure compounds was performed on a PS1 column (Molecular filtration Chromatography, column provided by Merck, Darmstadt, Germany) using acetonitrile as solvent under isocratic conditions. Every fraction was dried by using a vacuum concentrator and the yield was determined.

The final product of this example is used for the above described examples 1 to 3 for determining biological activities.

The path information, giving the details for the overall isolation process, is given in Table 4. For all subsequent separations in preparative scale, a HPLC-setup was used comprising reversed phase separation columns with capacity for up to 200 mg material per separation. The gradients for elution were chosen according to the separation problem (Table 3). Generally the systems were based on Water/Acetonitrile mixtures. On a case-wise basis, the final separation step for the isolation of pure compounds was performed on a PS1 column (Molecular filtration Chromatography, column provided by Merck, Darmstadt, Germany) using acetonitrile as solvent under isocratic conditions. Every fraction was dried (at 50° C. temperature setting) by using a vacuum concentrator and the yield was determined. For the control of every single fractionation step the resulting fractions were analyzed by HPLC-UV-ELSD as described above.

TABLE 3

History of isolation

| Procedure number | Starting fraction (s) | Conditions of separations | Product of separation step [COI] | retention time [min], yields [mg] |
|---|---|---|---|---|
| 2 | TC 2 (2) | Nucleodur 100-5 C18ec, 250 × 21 mm, Flow: 20 ml/min | TC 3 (4) | 16-18 49 |
| 3 | TC 2 (3) | Nucleodur 100-5 C18ec, 250 × 21 mm, Flow: 20 ml/min | TC 4 (2)-TC 4 (5) | 19-22 80 |
| 4 | TC 2 (4) | Nucleodur 100-5 C18ec, 250 × 21 mm, Flow: 20 ml/min | TC 5 (2) | 18-22 39 |
| 5 | TC 2 (6) | Nucleodur 100-20 C18ec, 130 × 40 mm, 20 ml/min | TC 6 (4) | 28-29 412 |
| 6 | TC 2 (7) | Nucleodur 100-20 C18ec, 130 × 40 mm, 20 ml/min | TC 7 (4 + 5) | 33-42 1182 |
| | | | TC 7 (7) | 45-48 378 |
| 7 | TC 2 (9 + 10) | Nucleodur 100-20 C18ec, 130 × 40 mm, 20 ml/min | TC 8 (2) | 31-34 474 |
| | | | TC 8 (5) | 40-43 813 |
| 8 | TC 2 (11) | Nucleosil 100-7 C18, 250 × 21 mm, 20 ml/min | TC 9 (2 + 3) | 21-25 110 |
| | | | TC 9 (5 + 6) | 26-27 78 |
| 10 | TC 2 (13) | Nucleosil 100-7 C18, 250 × 21 mm, 20 ml/min | TC 11 (3) | 25-26 17 |
| | | | TC 11 (5)-TC 11 (7) | 26.5-28 17 |
| 12 | TC 3 (4) | LiChrogel PS1 (10 µm), 250 × 25 mm, 4 ml/min | TC 13 (3)-TC 13 (7) | 14-29 41 |
| 13 | TC 5 (2) | LiChrogel PS1 (10 µm), 250 × 25 mm, 4 ml/min | TC 14 (1)-TC 14 (3) | 0-22 26 |
| 15 | TC 9 (3) | Nucleodur 100-5 C18ec, 250 × 10 mm, 8 ml/min | TC 16 (3) | 33.5-34 13 |

TABLE 3-continued

History of isolation

| Procedure number | Starting fraction(s) | Conditions of separations | Product of separation step [COI] | retention time [min], yields [mg] |
|---|---|---|---|---|
| 16 | TC 9 (5 + 6) | Nucleosil 100-7 C18, 250 × 21 mm, 20 ml/min | TC 17 (6 + 7) | 18-20.5 25 |
| 19 | TC 5 (4) | Nucleodur 100-20 C18ec, 250 × 21 mm, Flow: 20 ml/min | TC 20 (3) [COI 4] | 21-22 89 |
| 20 | TC 7 (4) | Nucleodur 100-20 C18ec, 250 × 21 mm, Flow: 20 ml/min | TC 21 (4) | 53-58 442 |
| 21 | TC 8 (2) | Nucleodur 100-20 C18ec, 250 × 21 mm, Flow: 20 ml/min | TC 22 (5) [COI 3] | 50-54 176 |
| 22 | TC 8 (5) | Nucleodur 100-20 C18ec, 250 × 21 mm, Flow: 20 ml/min | TC 23 (3) | 49-51 225 |
| 25 | TC 7 (5) | Nucleosil 100-7 C18, 250 × 21 mm, 20 ml/min | TC 26 (5) | 20.5-21.5 42 |
| 27 | TC 21 (4) | Nucleosil 100-7 C18, 250 × 21 mm, 20 ml/min | TC 28 (2) [COI 7] | 12-13.5 131 |
| 28 | TC 23 (3) | GL Sciences Inc. Inertsil ODS-3, 250 × 50 mmm, 20 ml/min | TC 29 (6) | 117-118 41 |
| 30 | TC 17 (6 + 7) | LiChrogel PS1 (10 μm), 250 × 25 mm, 4 ml/min | TC 31 (3) [COI 10] | 31-33 5 |

TABLE 4

Solvent and gradient conditions of the procedures of Table 3

| Procedure No. | Solvent System employed | Linear Gradient |
|---|---|---|
| 2; 3; 4 | Solvent A: H2O + 0.1% TFA | 0% B to 30% B in 30 min |
| | Solvent B: Methanol + 0.1% TFA | 30% B to 100% B in 5 min |
| 5; 6 | Solvent A: H2O + 0.1% TFA | 10% B to 50% B in 60 min |
| | Solvent B: Methanol + 0.1% TFA | 50% B to 100% B in 10 min |
| 7 | Solvent A: H2O + 0.1% TFA | 20% B to 50% B in 60 min |
| | Solvent B: Methanol + 0.1% TFA | 50% B to 100% B in 10 min |
| 8 | Solvent A: H2O | 10% B to 60% B in 30 min |
| | Solvent B: Acetonitrile | 60% B to 100% B in 5 min |
| 9; 10 | Solvent A: H2O | 20% B to 70% B in 30 min |
| | Solvent B: Acetonitrile | 70% B to 100% B in 5 min |
| 11 | Solvent A: H2O | 30% B to 70% B in 30 min |
| | Solvent B: Acetonitrile | 70% B to 100% B in 5 min |
| 12; 13; 29; 30; 31 | Solvent A: Acetontrile | Isocratic elution |
| 14; 15 | Solvent A: H2O | 0% B to 30% B in 30 min |
| | Solvent B: Acetonitrile | 30% B to 100% B in 5 min |
| 16; 17; 18 | Solvent A: H2O | 30% B to 60% B in 30 min |
| | Solvent B: Acetonitrile | 60% B to 100% B in 5 min |
| 19; 20; 21 | Solvent A: H2O + 0.1% TFA | 20% B to 40% B in 60 min |
| | Solvent B: Methanol + 0.1% TFA | 40% B to 100% B in 10 min |
| 22 | Solvent A: H2O + 0.1% TFA | 20% B to 40% B in 60 min |
| | Solvent B: Acetonotrile + 0.1% TFA | 40% B to 100% B in 10 min |
| 23; 24 | Solvent A: H2O | 0% B to 25% B in 30 min |
| | Solvent B: Acetonotrile | 25% B to 100% B in 5 min |
| 25; 26 | Solvent A: H2O | 10% B to 30% B in 30 min |
| | Solvent B: Acetonotrile | 30% B to 100% B in 5 min |
| 27 | Solvent A: H2O | 15% B to 25% B in 30 min |
| | Solvent B: Acetonotrile | 25% B to 100% B in 5 min |
| 28 | Solvent A: H2O | 15% B to 30% B in 60 min |
| | Solvent B: Acetonotrile | 30% B to 40% B in 5 min |
| 32 | Solvent A: H2O | 15% B to 30% B in 30 min |
| | Solvent B: Acetonotrile | 30% B to 100% B in 5 min |

The separation campaign resulted in 4 pure compounds: TC 20 (3), TC 22 (5), TC 28 (2) and TC 31 (3). Details for the isolated compounds can be found in Table 5.

Further compounds found in an analogous way are also disclosed in the following table:

TABLE 5
| [Compound of Interest (COI) No.] | Retention time [min.] | Structure | Mol. weight | Compound name (CAS RN) |
|---|---|---|---|---|
| 215 mg TC 20 (3) [COI 4] | 7.74 (anal. method) 9.51 (derep. method) | 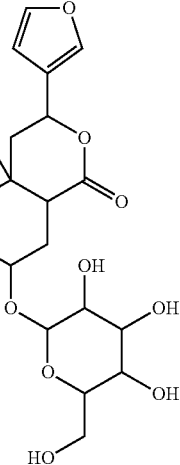 | 552.52 | Borapetoside B (104901-05-5) |
| 131 mg TC 28 (2) [COI 7] | 8.37 (anal. method) 10.22 (derep. method) | 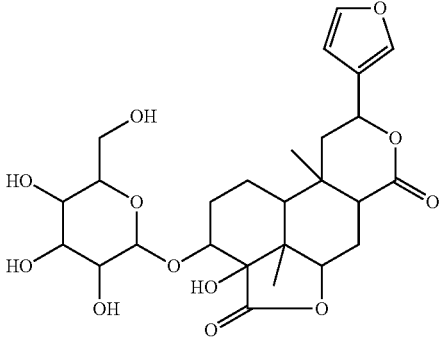 | 538.54 | Borapetoside A (100202-29-7) |
| 176 mg TC 22 (5) [COI 3] | 10.40 (anal. method) 12.16 (derep. method) | 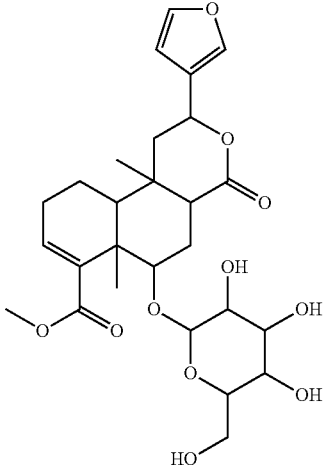 [SMILES: COC(=O)C1=CCCC2C3(C)CC(c4ccoc4)OC(=O)C3CC(OC3OC(CO)C(O)C(O)C3O)C12C] | 536.57 | Borapetoside C Tinocrisporide (145459-46-7) |

TABLE 5-continued

Isolated pure compounds from *Tinospora crispa* roots

| [Compound of Interest (COI) No.] | Retention time [min.] | Structure | Mol. weight | Compound name (CAS RN) |
|---|---|---|---|---|
| 6.7 mg TC 31 (3) [COI 10] | 12.71 (anal. method) 14.49 (derep. method) | 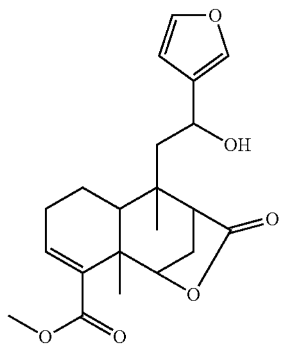 [SMILES: COC(=O)C1=CCCC2C(C)(CC(O)c3ccoc3)C3CC(OC3=O)C12C] | 293.31 | (176519-80-5) |
| [COI 1] | 9.10 (derep. method) | 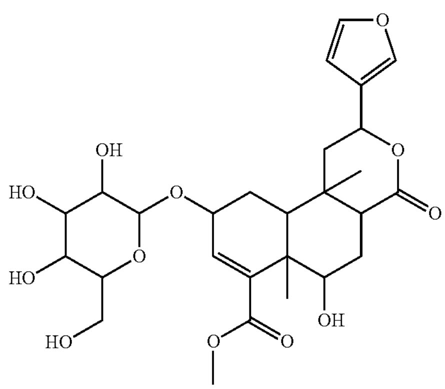 | 552.56 | |
| [COI 6] | 9.92 (derep. method) | 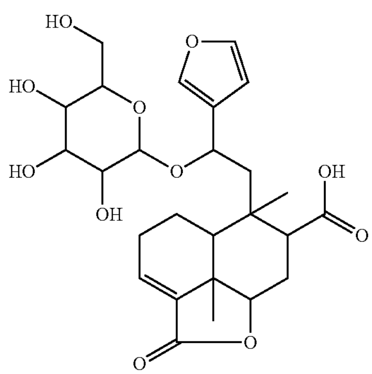 | 522.54 | |
| [COI 2] | 10.63 (derep. method) | 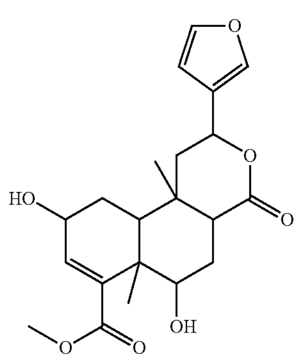 [SMILES: COC(=O)C1=CC(O)CC2C3(C)CC(c4ccoc4)OC(=O)C3CC(O)C12C] | 390.42 | Borapetol (104901-06-6) (176590-74-4) |

TABLE 5-continued

Isolated pure compounds from *Tinospora crispa* roots

| [Compound of Interest (COI) No.] | Retention time [min.] | Structure | Mol. weight | Compound name (CAS RN) |
|---|---|---|---|---|
| [COI 5] | 11.02 (derep. method) | 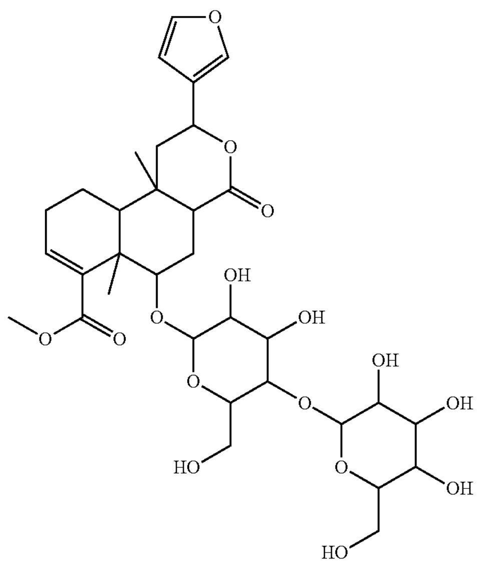 [SMILES: COC(=O)C1=CCCC2C3(C)CC(c4ccoc4)OC(=O)C3CC(OC3OC(CO)C(OC4OC(CO)C(O)C(O)C4O)C(O)C3O)C12C] | 698.70 | |
| [COI 8] | 12.11 (derep. method) | 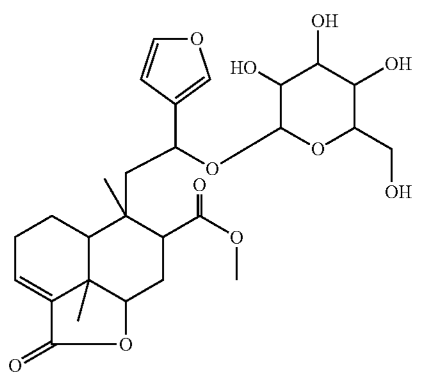 | 536.56 | |

The following Table 5b gives the IUPAC names for the Compounds of Interest:

IUPAC Names:

| [COI] | IUPAC Name |
|---|---|
| 1 | methyl 2-(furan-3-yl)-6-hydroxy-6a,10b-dimethyl-4-oxo-9-(3,4,5-trihydroxy-6-(hydroxymethyl)tetrahydro-2H-pyran-2-yloxy)-2,4,4a,5,6,6a,9,10,10a,10b-decahydro-1H-benzo[f]isochromene-7-carboxylate |
| 2 | methyl 2-(furan-3-yl)-6,9-dihydroxy-6a,10b-dimethyl-4-oxo-2,4,4a,5,6,6a,9,10,10a,10b-decahydro-1H-benzo[f]isochromene-7-carboxylate |
| 3 | methyl 2-(furan-3-yl)-6a,10b-dimethyl-4-oxo-6-(3,4,5-trihydroxy-6-(hydroxymethyl)tetrahydro-2H-pyran-2-yloxy)-2,4,4a,5,6,6a,9,10,10a,10b-decahydro-1H-benzo[f]isochromene-7-carboxylate |
| 4 | methyl 2-(furan-3-yl)-9-hydroxy-6a,10b-dimethyl-4-oxo-6-(3,4,5-trihydroxy-6-(hydroxymethyl)tetrahydro-2H-pyran-2-yloxy)-2,4,4a,5,6,6a,9,10,10a,10b-decahydro-1H-benzo[f]isochromene-7-carboxylate |
| 5 | methyl 6-(3,4-dihydroxy-6-(hydroxymethyl)-5-(3,4,5-trihydroxy-6-(hydroxymethyl)tetrahydro-2H-pyran-2-yloxy)tetrahydro-2H-pyran-2-yloxy)-2-(furan-3-yl)-6a,10b-dimethyl-4-oxo-2,4,4a,5,6,6a,9,10,10a,10b-decahydro-1H-benzo[f]isochromene-7-carboxylate |
| 6 | 6-(2-(furan-3-yl)-2-(3,4,5-trihydroxy-6-(hydroxymethyl)tetrahydro-2H-pyran-2-yloxy)ethyl)-2a1,6-dimethyl-2-oxo-2a1,4,5,5a,6,7,8,8a-octahydro-2H-naphtho[1,8-bc]furan-7-carboxylic acid |

-continued

| [COI] | IUPAC Name |
|---|---|
| 7 | 9-(furan-3-yl)-3a-hydroxy-3a1,10a-dimethyl-3-(3,4,5-trihydroxy-6-(hydroxymethyl)tetrahydro-2H-pyran-2-yloxy)decahydroisobenzofuro[7,1-fg]isochromene-4,7(3a1H,5aH)-dione |
| 8 | methyl 6-(2-(furan-3-yl)-2-(3,4,5-trihydroxy-6-(hydroxymethyl)tetrahydro-2H-pyran-2-yloxy)ethyl)-2a1,6-dimethyl-2-oxo-2a1,4,5,5a,6,7,8,8a-octahydro-2H-naphtho[1,8-bc]furan-7-carboxylate |
| 10 | (E)-methyl 2-(2-(furan-3-yl)-2-hydroxyethyl)-2-methyl-11-oxo-10-oxatricyclo[7.2.1.0$^{3,8}$]dodec-6-ene-7-carboxylate |

Example 3

Optimized Extract

Pure samples of 6 main components were used for calibration purposes.

TABLE 6

| | Peak area UV (TIC) | | | | | |
|---|---|---|---|---|---|---|
| Conc. [mg/ml] | IMD-002993 [COI 6] | IMD-013076 [COI 3] | IMD-013089 [COI 4] | IMD-013090 [COI 7] | IMD-013091 [COI 5] | IMD-013092 [COI 8] |
| 0.01 | 5303 | 4586 | 2710 | 3086 | 3029 | 9138 |
| 0.02 | 14816 | 10273 | 7360 | 4904 | 6788 | 15639 |
| 0.05 | 28511 | 25200 | 20441 | 11321 | 19218 | 36653 |
| 0.1 | 59518 | 58066 | 59688 | 21240 | 32947 | 75998 |
| 0.2 | 105776 | 113356 | 119748 | 44208 | 65106 | 151698 |
| 0.5 | 235684 | 357840 | 273805 | 93484 | 161145 | 344389 |
| 1* | 433089 | 485106 | 430440 | 243323 | 373605 | 571663 |
| 2* | 682879 | 763800 | 642777 | 276783 | 486384 | 834238 |
| Linear regression formula* | y = 464440x + 6816.8 | y = 721016x − 10862 | y = 558071x − 1225 | y = 185475x + 2504.3 | y = 320474x + 829.01 | y = 686786x + 4857.1 |
| $R^2$ | R2 = 0.9966 | R2 = 0.9935 | R2 = 0.9967 | R2 = 0.9954 | R2 = 0.9996 | R2 = 0.9984 |

*For the calculation of the linear regression the peak areas for the 2000 µg/ml and 1000 µg/ml measurements were not considered as the graphs were not linear any more in these concentration ranges.

20 g of dry crawling roots powder prepared as described in the above example were extracted under the conditions described in Table 7 with the aid of ultra sonification. The extracts were separated by filtration from the plant material and evaporated to dryness under reduced pressure at 50° C. The extract yields were determined. The dry extracts were dissolved in methanol to a final concentration of 10 mg/ml and subjected to HPLC-UV-MS-ELSD analyses using the gradient (which is described in the following paragraph) with an injection volume of 5 µl.

TABLE 7

Extraction methods and yields of the obtained extracts

| Sample name | Ground leaves [g] | Extraction method | Extract yield [mg] |
|---|---|---|---|
| extract 2 | 20 | 100% water, 30 min, 40° C. | 468 |
| extract 3 | 20 | Ethanol-water 30:70, 30 min, 40° C. | 839 |
| extract 4 | 20 | Ethanol-water 70:30, 30 min, 40° C. | 1661 |
| extract 5 | 20 | Ethanol-water 95:5, 30 min, 40° C. | 357 |
| extract 6 | 20 | 100% water; 30 min reflux at 95° C. | 328 |

HPLC-UV-MS-ELSD Dereplication Set-Up and Method:

LC-UV-MS analyses were performed using an Agilent HP1100 (Agilent, Waldbronn, Germany) liquid chromatograph coupled with a Waters LCT mass spectrometer (Waters Corporation, Milford, Mass., USA) in the positive and negative electrospray ionization (ESI) mode and an evaporative light scattering detector (ELSD; ERC GmbH, Riemerling, Germany). A Waters symmetry column (Waters Symmetry® C18, 3.5 µm, 2.1 mm×150 mm) was used as stationary phase with a flow rate of 0.4 ml/min at 40° C. Mobile phase A: 0.1% Formic acid in water, mobile phase B: 0.1% Formic acid in acetonitrile; gradient: 0-1 min. 98% A, from 1-21 min. to 100% B, from 21-27 min 100% B. The UV/vis spectra were recorded between 200-500 nm, the LC-MS spectra were recorded in the range of molecular weights between 160 and 1.600 U.

Extract 4 (70% Ethanolic Extract)

20 g milled roots of T. crispa were extracted once with 100 ml ethanol-water 70:30 at 40° C. for 30 min using ultrasound. The extracts were separated by filtration from the plant material and evaporated to dryness. The extract yield was 1661 g. The dry extract was dissolved in methanol to a final concentration of 10 mg/ml and subjected to HPLC-UV-MS-ELSD analyses using the standard dereplication gradient with an injection volume of 5 µl.

The extract yield obtained with the selected extraction method was very high (compared to the other extraction methods used). The compounds of interest (COIs) identified in the dereplication analysis (COI 6, COI 3, COI 4, COI 7, COI 5, COI 8) were available in the amounts of 5.3 mg/ml (COI 6) to 47.3 mg/ml (COI 4). The content was less than in the ethanol-water 95:5 extract but due to much larger extracts amounts the total yield of COIs was higher in the ethanol-water 70:30 extract.

Extract 6 (Hot Water Extract)

20 g milled roots of *T. crispa* were dissolved in 100 ml water and extracted at 95° C. for 30 min under reflux. The extracts were separated by filtration from the plant material and evaporated to dryness. The extract yield was 328 g. The dry extract was dissolved in methanol to a final concentration of 10 mg/ml and subjected to HPLC-UV-MS-ELSD analyses using the standard dereplication gradient with an injection volume of 5 μl. The COIs identified in the dereplication analysis (COI 6, COI 3, COI 4, COI 7, COI 5, COI 8) were available in the amounts of 1.6 mg/ml (COI 6) to 40.3 mg/ml (C014).

The absolute yields of the COIs are presented in Table 8.

TABLE 8

Calculated contents of COIs in the prepared extracts of *T. crispa* (Concentration of compounds [mg/g extract])

| Sample | [COI 6] | [COI 3]* | [COI 4] | [COI 7] | [COI 5] | [COI 8]* |
|---|---|---|---|---|---|---|
| extract 2 | 0.79 | 21.17 | 32.99 | 10.16 | 6.30 | 19.93 |
| extract 3 | 7.25 | 32.36 | 48.03 | 18.85 | 10.63 | 31.69 |
| extract 4 | 5.32 | 35.10 | 47.31 | 18.51 | 17.48 | 34.56 |
| extract 5 | 1.59 | 50.84 | 63.50 | 16.93 | 27.57 | 51.08 |
| extract 6 | 1.64 | 25.73 | 40.35 | 12.90 | 10.67 | 24.72 |

*Due to similar retention times the peak at RT 12.2 min can either be [COI 3] IMD-013076 or [COI 8] IMD-013092 or a mixture thereof.

Example 4

Biological Evaluation

Radioligand Binding Assay:

The inhibition of specific binding of 0.2 nM [$^3$H] LTB4 by test compounds is investigated in human myeloid U937 cells performed as described by Winkler (J Pharmacol Exp Ther.; 246(1): 204-10, 1988). As benchmark compound non-radioligated LTB4 is used (IC50 0.2; Ki 0.05 nM). From dose-dependent inhibition of specific LTB4 binding it can be concluded that test items are capable to bind to and to interact with LTB4 receptors.

A) Recombinant Cell Assay (Human BLT2 Receptor)

The BLT2 assay conducted was a functional cell based assay, with transiently transfected HEK293T cells (Transfection: with chimeric G protein Gαqi5; Minami et al, "Analysis of the effects of halothane on Gi-coupled muscarinic M2 receptor signal" Pharmacology (2004) 72: 205-12). The dose-dependant stimulation of intercellular calcium flux upon treatment with test item was measured in the antagonist read out mode with EC80 pre-stimulation of the receptor using the agonist LTB4. The EC80 pre-stimulation dose was determined in a control experiment using an 8 point dose response curve with the agonist Leukotriene B4 (LTB4), the dose was determined to 2*10E-6 M LTB4. The test items were measured subsequently in the antagonist mode as described above in a concentration of 10 μM (pure compounds) or 15 μg/ml (extracts and/or mixtures).

This assay was performed by Multispan, Inc., Hayward (CA, USA) under the catalog no C1272, the assay principle is outlined by Yokomizo (J Exp Med (2000) 192:421-432).

Material
    Cells: BLT2 HEK293T cells transiently transfected with chimeric G protein Gαqi5
    Compounds: Test compounds dissolved in DMSO at a concentration of 10 mM or 100 mg/mL. Leukotriene B4 (LTB4) was used as control agonist (Cayman Chemical Company, Ann Arbor, Mich., USA; Catalogue #20110).
    Calcium assay kit: FLIPR Calcium 4 Assay Kit (Molecular Devices R8142)
    Instrument: FlexStation III (Molecular Devices)

Methods

Calcium assay: Cells were seeded in 384-well plates at appropriate densities and cultured overnight. Calcium assays were conducted according to the manufacturer's protocol using Molecular Devices FLIPR Calcium 4 Assay kit. Calcium 4 dye loading buffer was added to the cells and incubated for one hour at 37° C. The test compounds were pre-incubated for 5 minutes at a final concentration of 10 μM or 15 μg/mL, respectively. Calcium flux was measured for 90 seconds with the respective agonist compound injected into the wells at 19th second. Agonist was used at a concentration in which maximum reaction was observed. The agonist LTB4 was added in concentration of 0.002 μM which results in blank positive control (e.g. 0.1% DMSO) in an 70% increase in RFU.

Data analysis: Calcium assay results are expressed as "RFU" (Relative Fluorescence Units) and are shown in the following table as "remaining % RFU against DMOS) (meaning % Increase in RFU after correction for DMSO and baseline). Two-tailed Student's t-test was used for treatment comparisons and statistic significance was defined as $p<0.05$.

Results:

| Sample name | remaining % RFU against DMSO [%] |
|---|---|
| [COI 4] | 78.6 |
| [COI 7] | 83.2 |
| [COI 5] | 79.7 |
| Extract 4 | 76.2 |

B) The compounds of the invention may be tested for antagonist activity at the LTB4 receptor. Compounds can be tested in vivo in animal models including for inflammation models (e.g. paw edema model, collagen-induced arthritis, EAE model of MS).

a) This Example illustrates the anti-inflammatory activity of the present compounds using a model of carrageenan induced paw edema (a model of inflammation, carrageenan).

A compound of this invention is dissolved in a suitable vehicle (e.g. 2% Tween 80/0.9% NaCl) and administered intraperitoneally at an appropriate dose (e.g. 30-300 mg/kg, preferably 100-300 mg/kg) half an hour before carrageenan (1% 0.1 ml/paw) challenge. Dosing volume is 10 ml/kg. The animals (e.g. rats, mice, rabbits or coneys, preferred rats) are conditioned to the environment. The chemicals can be obtained commercially: Carrageenan (e.g. from TCI, Japan); Pyrogen free saline (e.g. from Astar, Taiwan); and Ibuprofen (e.g. from ICN BioMedicals, USA), or other positive controls e.g. like Acetylsalicylic acid (AAS), hydrocortisone. Common Equipment can be used (for example Glass syringe 1 ml and 2 ml (Mitsuba, Japan); Hypodermic needle 24 G*1" (Top Corporation, Japan); Plethysmometer #7150 (UGO Basile, Italy); and Water cell 25 mm Diameter, #7157 (UGO Basile, Italy).

Method:

Test substance (Example) is administered IP (100 and 300 mg/kg), or vehicle, or Ibuprofen (100 mg/kg) to 4 groups of 8 Sprague Dawley male rats weighing 160 to 180 gms 30 minutes before hind paw injection of carrageenan (0.1 ml of 1% suspension intraplantar). Hind paw edema, as a measure of inflammation, is recorded 1, 2, 3 and 4 hours after carrageenan administration using a plethysmometer with water cell.

The invention claimed is:

1. A method of treatment of an inflammatory disease or condition in a subject, the method comprising: administering at least one compound of formula I or a pharmaceutically acceptable salt and/or solvate thereof, respectively, with or without a carrier to a subject having the inflammatory disease or condition; the at least one compound of formula I each being a purified compound as follows:

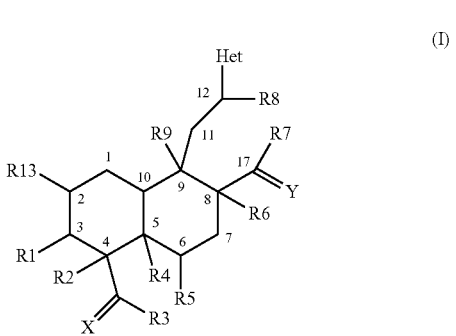

(I)

wherein
R1 is OR10 wherein R10 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
R2 is hydrogen, hydroxy, or etherified or esterified hydroxy;
or R1 and R2 together form a double bond;
R3 is hydroxy or etherified or esterified hydroxy;
R4 is $C_1$-$C_8$-alkyl;
R5 is OR11 wherein R11 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
or R3 and R5 together with their bonds form —O— or —S—;
R7 is hydroxy or etherified or esterified hydroxy;
or R5 and R7 together with their bonds form —O— or S—;
R6 is hydrogen, hydroxy or etherified or esterified hydroxy;
R8 is OR12 wherein R12 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
or R7 and R8 together with their bonds form —O— or —S—;
R9 is $C_1$-$C_8$-alkyl;
R13 is hydrogen or OR14 wherein R14 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
X is O or S;
Y is O or S;
and Het is an unsaturated, partially saturated or saturated heterocyclyl with 4 to 8 ring atoms of which 1 or two are oxygen, which heteroaryl is unsubstituted or substituted with one or more moieties independently selected from the group consisting of hydroxy, etherified or esterified hydroxy;
in free form, in the form of a salt, in the form of a tautomer, and/or in the form of a solvate.

2. The method of claim 1, wherein the at least one compound of the formula I in free form, in the form of a salt, in the form of a tautomer, and/or in the form of a solvate, includes:
R1 is OR10 where R10 is hydrogen or a hexose radical bound via one of its oxygen atoms;
R2 is hydroxy;
or R1 and R2 together form a double bond;
R3 is OH or O—$CH_3$;
R4 is methyl;
R5 is hydroxy or OR11 with R11=hexose radical bound via one of its oxygen atoms;
or R3 and R5 together with their bonds form —O— forming together with the atoms to which they are bound a lactone ring;
R6 is H;
R7 is OH or O—$CH_3$;
or R5 and R7 together with their bonds form —O— forming together with the atoms to which they are bound a lactone ring;
R8 is hydroxy or OR12 wherein R12 is hydrogen or a hexose radical bound via one of its oxygen atoms;
or R7 and R8 together with their bonds form —O— forming together with the atoms to which they are bound a lactone ring;
R9 is methyl;
R13 is hydrogen or OR14 wherein R14 is hydrogen or a hexose radical bound via one of its oxygen atoms;
X is O;
Y is O;
and Het is furan-3-yl or 2(5H)-furanon-3-yl or 5-hydroxy-2(5H)-furanon-3-yl,
in free form, in the form of a salt, in the form of tautomers, and/or in the form of a solvate.

3. The method of claim 1, wherein the at least one A compound of the formula I is selected from the group of compounds with the formulae:

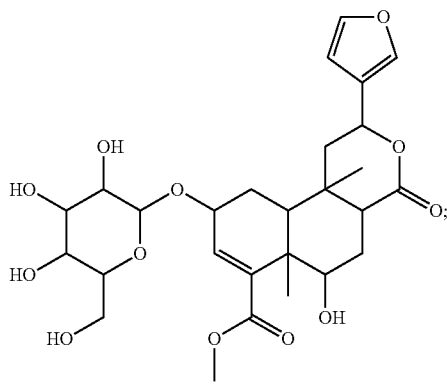

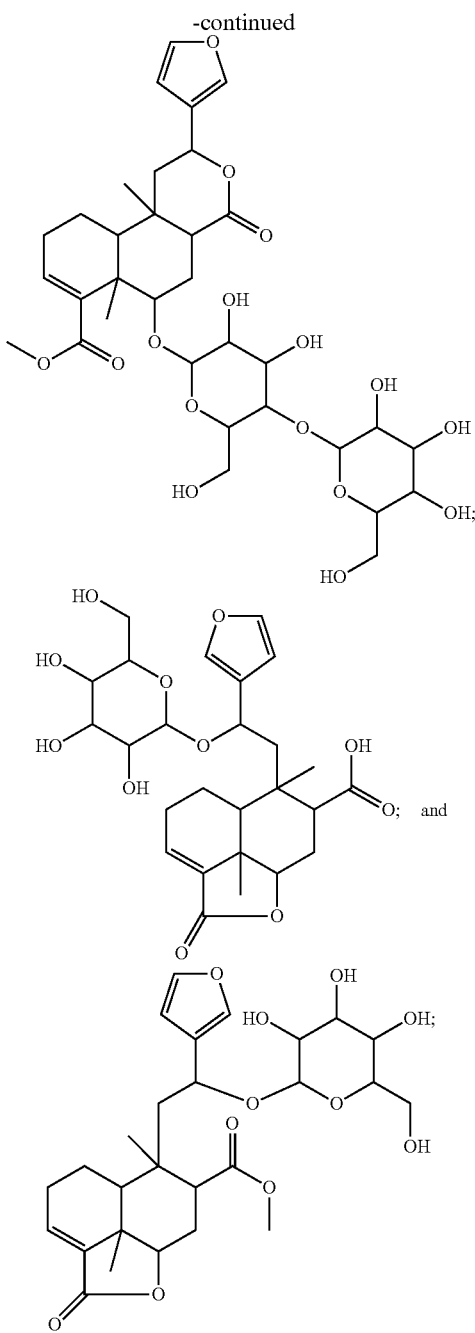

in free form, in the form of a salt, in the form of tautomers, and/or in the form of a solvate, respectively.

4. The method of claim 1, wherein the subject is administered a formulation comprising a carrier having the at least one compound of the formula I or a pharmaceutically or nutraceutically acceptable salt, and/or solvate thereof.

5. The method according to claim 1, wherein the inflammatory diseases or conditions are one or more selected from the group consisting of autoimmune disease related inflammation, inflammation associated with the pathophysiological condition of other diseases or substances, and allergy.

6. The method according to claim 5, where the inflammatory disease or condition is selected from the group consisting of an inflammatory disease or condition a) of the airways;
b) of the eye;
c) of skin;
d) of the gastrointestinal tract, immune disorders of the gut, or bowel irregularity;
e) of the bone, muscle or joints;
f) of organs or tissues;
g) allergy;
or any combination of two or more such diseases or conditions.

7. A method of treatment of an inflammatory disease or condition, comprising administering to an individual having the inflammatory disease or condition that is in need of such treatment a pharmaceutically or nutraceutically effective amount of a compound, a mixture of compounds;
the compounds of formula I each being a purified compound without a carrier as follows:

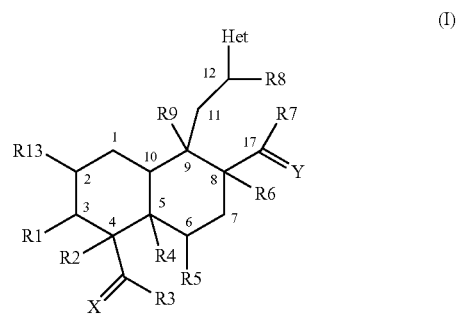

wherein
R1 is OR10 wherein R10 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
R2 is hydrogen, hydroxy, or etherified or esterified hydroxy;
or R1 and R2 together form a double bond;
R3 is hydroxy or etherified or esterified hydroxy;
R4 is $C_1$-$C_8$-alkyl;
R5 is OR11 wherein R11 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
or R3 and R5 together with their bonds form —O— or —S—;
R7 is hydroxy or etherified or esterified hydroxy;
or R5 and R7 together with their bonds form —O— or S—;
R6 is hydrogen, hydroxy or etherified or esterified hydroxy;
R8 is OR12 wherein R12 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
or R7 and R8 together with their bonds form —O— or —S—;
R9 is $C_1$-$C_8$-alkyl;
R13 is hydrogen or OR14 wherein R14 is hydrogen, the moiety of a carbohydrate having 2 to 30 carbon atoms bound via one of its oxygen atoms, $C_1$-$C_8$-alkoxy, $C_1$-$C_8$-alkanoyloxy or benzoyloxy;
X is O or S;
Y is O or S;
and Het is an unsaturated, partially saturated or saturated heterocyclyl with 4 to 8 ring atoms of which 1 or two are oxygen, which heteroaryl is unsubstituted or substituted with one or more moieties independently selected from the group consisting of hydroxy, etherified or esterified hydroxy;

in free form, in the form of a salt, in the form of a tautomer, and/or in the form of a solvate.

* * * * *